United States Patent
Ovokaitys et al.

(10) Patent No.: US 10,202,598 B2
(45) Date of Patent: *Feb. 12, 2019

(54) METHODS AND SYSTEMS FOR GENERATION, USE, AND DELIVERY OF ACTIVATED STEM CELLS

(71) Applicants: Todd Frank Ovokaitys, Carlsbad, CA (US); John Scott Strachan, Edinburgh (GB)

(72) Inventors: Todd Frank Ovokaitys, Carlsbad, CA (US); John Scott Strachan, Edinburgh (GB)

(73) Assignee: Todd Frank Ovokaitys, Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/349,886

(22) Filed: Nov. 11, 2016

(65) Prior Publication Data

US 2017/0233717 A1 Aug. 17, 2017

Related U.S. Application Data

(63) Continuation-in-part of application No. 14/726,457, filed on May 30, 2015, now Pat. No. 9,999,785.
(Continued)

(51) Int. Cl.
*C12N 13/00* (2006.01)
*A61K 35/28* (2015.01)
(Continued)

(52) U.S. Cl.
CPC .............. *C12N 13/00* (2013.01); *A61K 35/28* (2013.01); *A61K 35/51* (2013.01); *A61K 41/00* (2013.01);
(Continued)

(58) Field of Classification Search
USPC ..................................................... 607/88–92
See application file for complete search history.

(56) References Cited

U.S. PATENT DOCUMENTS 3,703,576 A   11/1972  Kitajima
4,840,174 A   6/1989   Gluckman
(Continued)

FOREIGN PATENT DOCUMENTS

EP   1011697          6/2000
EP   1292134 A2 *     3/2003   ......... G02B 27/0927
(Continued)

OTHER PUBLICATIONS

Taylor et al., "Banking on human embryonic stem cells: estimating the number of donor cell lines needed for HLA matching", Lancet, Dec. 10, 2005; 366: pp. 2019-2025.*
(Continued)

*Primary Examiner* — Christopher A Flory
*Assistant Examiner* — Vynn Huh
(74) *Attorney, Agent, or Firm* — Novel IP

(57) ABSTRACT

Harvested stem cells are activated by treating them with an amplitude modulated laser beam having a wavelength lying in the range of 405 to 980 nanometers. The frequency of the laser beam is modulated within a range of 8 to 12 MHz. Using the activated stem cells, tissue can be repaired and regenerated by preparing the unactivated stem cells, treating the unactivated stem cells with an amplitude modulated laser beam having a pre-determined frequency for obtaining activated stem cells, administering the activated stem cells into a body containing the tissue, and using a homing beam to guide the activated stem cells within the body to the location of the tissue.

20 Claims, 8 Drawing Sheets

Related U.S. Application Data

(60) Provisional application No. 62/321,781, filed on Apr. 13, 2016, provisional application No. 62/254,220, filed on Nov. 12, 2015, provisional application No. 62/006,034, filed on May 30, 2014.

(51) Int. Cl.
 *A61K 35/51* (2015.01)
 *A61K 41/00* (2006.01)
 *A61N 5/06* (2006.01)
 *A61N 5/067* (2006.01)

(52) U.S. Cl.
 CPC .......... *A61N 5/062* (2013.01); *A61N 5/0622* (2013.01); *A61N 2005/067* (2013.01); *A61N 2005/0626* (2013.01); *A61N 2005/0659* (2013.01); *A61N 2005/0662* (2013.01)

(56) References Cited

U.S. PATENT DOCUMENTS

| | | | |
|---|---|---|---|
| 5,571,797 | A | 11/1996 | Ohno |
| 5,874,266 | A | 2/1999 | Palsson |
| 6,064,500 | A | 5/2000 | Strachan |
| 6,763,607 | B2 | 7/2004 | Beyerinck |
| 6,811,564 | B1 | 11/2004 | Strachan |
| 7,294,508 | B2 | 11/2007 | Parikh |
| 7,427,502 | B2 | 9/2008 | Gostjeva |
| 7,674,620 | B2 | 3/2010 | Totey |
| 7,829,335 | B2 | 11/2010 | Inoue |
| 8,173,632 | B2 | 5/2012 | Ovokaitys |
| 8,313,477 | B2 | 11/2012 | See |
| 8,377,989 | B2 | 2/2013 | Ovokaitys |
| 8,404,733 | B2 | 3/2013 | Ovokaitys |
| 8,748,178 | B2 | 6/2014 | Egli |
| 8,788,213 | B2 | 7/2014 | Bright |
| 2002/0034546 | A1 | 3/2002 | Ullah |
| 2002/0058952 | A1 | 5/2002 | Weber |
| 2003/0163931 | A1 | 9/2003 | Beyerinck |
| 2004/0204746 | A1* | 10/2004 | Ovokaitys ............... A61N 5/00 607/89 |
| 2004/0230257 | A1 | 11/2004 | Ovokaitys |
| 2004/0239044 | A1 | 12/2004 | Blatter |
| 2004/0247671 | A1 | 12/2004 | Prescott |
| 2005/0170506 | A1 | 8/2005 | Sayre |
| 2005/0188921 | A1 | 9/2005 | Malone |
| 2006/0013869 | A1 | 1/2006 | Ignatious |
| 2006/0129210 | A1 | 6/2006 | Cantin |
| 2007/0003615 | A1 | 1/2007 | Jenkins |
| 2007/0154465 | A1 | 7/2007 | Kharazi |
| 2007/0231307 | A1 | 10/2007 | Tankovich |
| 2008/0064099 | A1 | 3/2008 | Parikh |
| 2008/0176332 | A1 | 7/2008 | Berns |
| 2008/0183162 | A1 | 7/2008 | Altshuler |
| 2009/0131376 | A1 | 5/2009 | Ovokaitys |
| 2009/0131710 | A1 | 5/2009 | Ovokaitys |
| 2010/0015576 | A1 | 1/2010 | Altshuler |
| 2010/0068141 | A1 | 3/2010 | Kaushal |
| 2012/0041521 | A1 | 2/2012 | Oron |
| 2012/0101479 | A1* | 4/2012 | Paspaliaris ............. A61K 35/12 604/522 |
| 2012/0129158 | A1 | 5/2012 | Berns |
| 2012/0215156 | A1 | 8/2012 | Ishikawa |
| 2012/0220641 | A1 | 8/2012 | Ovokaitys |
| 2012/0258451 | A1 | 10/2012 | Klimanskaya |
| 2014/0004601 | A1 | 1/2014 | Lim |
| 2014/0093482 | A1 | 4/2014 | Paspaliaris |
| 2014/0128800 | A1* | 5/2014 | Kim ................... C07K 14/7158 604/20 |
| 2014/0200503 | A1 | 7/2014 | Centurion |
| 2014/0273207 | A1 | 9/2014 | Chan |
| 2014/0303546 | A1 | 10/2014 | Badiavas |
| 2014/0377831 | A1 | 12/2014 | Ho |
| 2015/0343234 | A1 | 12/2015 | Ovokaitys |
| 2015/0353433 | A1 | 12/2015 | Ovokaitys |
| 2017/0233717 | A1 | 8/2017 | Ovokaitys |

FOREIGN PATENT DOCUMENTS

| | | |
|---|---|---|
| EP | 1421181 | 5/2004 |
| EP | 1892290 | 2/2008 |
| EP | 2248888 | 11/2010 |
| JP | 2008194055 | 8/2008 |
| RU | 2291703 | 1/2007 |
| SG | 172471 | 7/2011 |
| WO | 1995029645 | 2/1995 |
| WO | 1996039489 | 2/1996 |
| WO | 1998042356 | 2/1998 |
| WO | 0100563 A1 | 1/2001 |
| WO | 2001068110 | 1/2001 |
| WO | 02059087 A1 | 8/2002 |
| WO | 2003018783 | 1/2003 |
| WO | 2003029402 | 1/2003 |
| WO | 03020291 A1 | 3/2003 |
| WO | 2004071435 A2 | 8/2004 |
| WO | 2004081172 | 9/2004 |
| WO | 2007014323 | 2/2007 |
| WO | 2007100614 | 9/2007 |
| WO | 2008013985 | 3/2008 |
| WO | 2008089292 | 7/2008 |
| WO | 2009050696 | 4/2009 |
| WO | 2009052246 A1 | 4/2009 |
| WO | 2009052248 A1 | 4/2009 |
| WO | 2010005557 | 1/2010 |
| WO | 2010124585 | 11/2010 |
| WO | 2010134007 | 11/2010 |
| WO | 2011100651 A1 | 8/2011 |
| WO | 2011109797 | 9/2011 |
| WO | 2012071393 | 5/2012 |
| WO | 2012122081 | 9/2012 |
| WO | 2012122081 A2 | 9/2012 |
| WO | 2012131558 | 10/2012 |
| WO | 2012178156 | 12/2012 |
| WO | 2013003557 A1 | 1/2013 |
| WO | 2013063406 | 5/2013 |
| WO | 2013141715 A1 | 9/2013 |
| WO | 2014185945 | 11/2014 |
| WO | 2015053694 | 4/2015 |
| WO | 2015184421 A1 | 12/2015 |
| WO | 2015187974 A1 | 12/2015 |
| WO | 2017083755 A1 | 5/2017 |

OTHER PUBLICATIONS

International Search Report for PCT/US16/61673, dated Mar. 2, 2017.
Ong, Wei-Kee et al., The activation of directional stem cell motility by green light-emitting diode irradiation, Dec. 19, 2012, Biomaterials, 34: pp. 1911-1920.
Office Action dated Nov. 3, 2016 for U.S. Appl. No. 14/726,457.
Office Action dated Jul. 21, 2017 for U.S. Appl. No. 14/726,457.
International Search Report for PCT/US15/33425, dated Sep. 29, 2015.
Gatrix, "Supplementing with Light." www.cam-mag.com, CAM Nov. 2012 (2012), enitre document [online] URL=<http://perfect-tp.dyndns-ip.com/DT/perfect/images/mg_cam.pdf>.
Office Action dated Dec. 27, 2017 for U.S. Appl. No. 14/726,457; (pp. 1-7).
Extended European Search Report for EP15799255.3, dated Feb. 1, 2018.
Notice of Allowance dated May 15, 2018 for U.S. Appl. No. 14/726,457 (pp. 1-7).
International Search Report for PCT/US15/34236, dated Sep. 18, 2015.
International Search Report for PCT/US11/24694, dated Apr. 25, 2011.
International Search Report for PCT/US04/03752, dated Sep. 7, 2006.

(56) References Cited

OTHER PUBLICATIONS

International Search Report for PCT/US08/80098, dated Feb. 20, 2009.
International Search Report for PCT/US08/80095, dated Dec. 16, 2008.

* cited by examiner

| Patient Details | EF baseline | EF I screening (3 Days) | EF II screening (7 Days) | EF III screening (30 Days) | EF IV screening (60 Days) | EF V screening (90 Days) |
|---|---|---|---|---|---|---|
| Patient 1 | 20% | 25% | 28% | 28% | 32% | 32% |
| Patient 2 | 25% | - | 28% | 33% | 33% | 44% |
| Patient 3 | 20% | 30% | 32% | 34% | 36-37% | 43% |
| Patient 4 | 23% | 23% | 27% | 22% | - | 28-29% |
| Patient 5 | 20% | 20% | 22% | 24% | 24% | 27% |
| Patient 6 | 20% | 23% | 23% | 24% | 27% | 28% |
| Patient 7 | 20% | 23% | 23% | 23% | 23% | 23% |
| Patient 8 | 23% | 25% | 26% | 27% | 30% | 32% |
| Patient 9 | 20% | 23% | 23% | 25% | 27% | 25% |
| Patient 10 | 22% | 23% | 25% | 25% | 25% | 25% |

FIG. 6

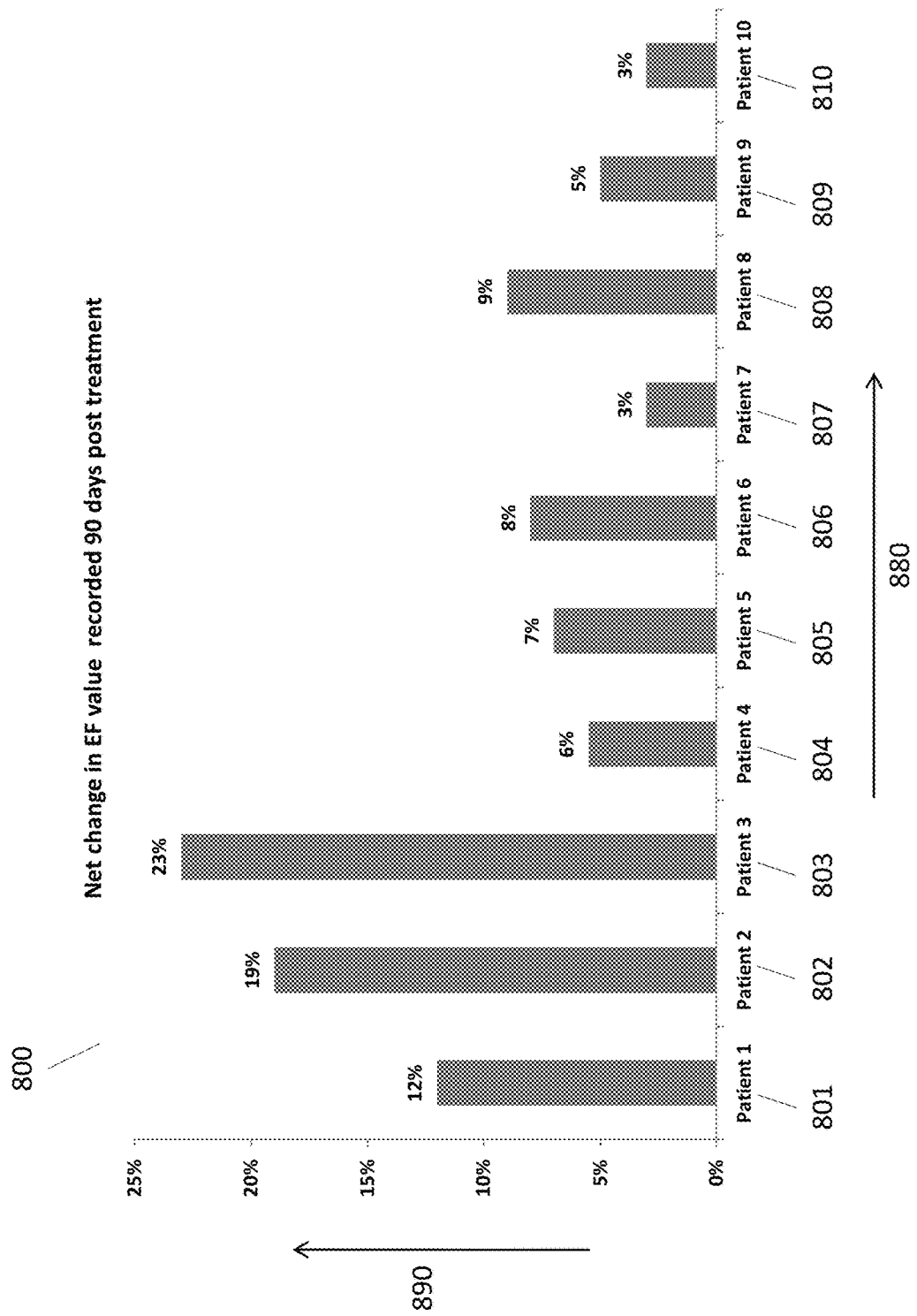

METHODS AND SYSTEMS FOR GENERATION, USE, AND DELIVERY OF ACTIVATED STEM CELLS

CROSS-REFERENCE

The present application relies on, for priority, the following U.S. Provisional Patent Applications, which are also herein incorporated by reference in their entirety:

U.S. Provisional Patent Application No. 62/321,781, entitled "Method and System for Generation and Use of Activated Stem Cells", and filed on Apr. 13, 2016; and, U.S. Provisional Patent Application No. 62/254,220, entitled "Method and System for Generation and Use of Activated Stem Cells", and filed on Nov. 12, 2015.

The present application is a continuation-in-part of U.S. patent application Ser. No. 14/726,457, of the same title, and filed on May 30, 2015, which, in turn, relies on U.S. Patent Provisional Application No. 62/006,034, filed on May 30, 2014, for priority.

The above-mentioned applications are herein incorporated by reference in their entirety.

FIELD

The present specification discloses methods and systems for activating stem cells and, in particular, the use of modulated ultra-rapid laser impulses to activate and guide stem cells.

BACKGROUND

While stem cells offer therapeutic potential for the replacement of damaged or degenerated cells, therapies have been limited by an inability to effectively and efficiently guide the stem cells to a target location in sufficient numbers to achieve the desired results. In the case of an active inflammatory condition, the stem cells may be naturally attracted to the target tissue to some degree, but, in general, there is a need to increase and improve the extent to which stem cells are actively guided and/or channeled to the target location. This is especially true when attempting to treat past healed injuries, such as the spinal cord after transection.

What is needed, therefore, is a method of delivering stem cells to a treatment region, and stimulating adherence, differentiation and integration.

SUMMARY

When applying an amplitude modulated laser beam, as described below, through a flask of Kg1a cells, it has been found that the cells unexpectedly line up in a string, the cells adhering to each other where the beam had been placed. Upon examination, the primitive cells line Kg1a, which has stem cell like features, was found to have increased its expression of the hematopoietic stem cell marker CD34. Upon further review, it was also realized that the nature of the modulated laser signal would be broadly stimulating to the cell adhesion and communication molecules known as alpha and beta integrins. Flow cytometry showed a variable yet significant increase in the measurement of beta 1, beta 2 and alpha 4 integrin molecules on the cell surface that peaked in 24 hours and declined after 48 hours. Visible observations were that cell-to-cell and cell to surface (of the flask) adhesion were markedly increased wherever the beam was directed in a flask of cells. Accordingly, it was determined that the stimulus increases migration and localization of stem cells, while also increasing cell adhesion molecule expression in stem cells. Additionally, tissue stimulated with such a resonant signal draws stem cells to where the beam is directed and favors the cells remaining in the tissue, which has also been stimulated to possess higher adhesion characteristics. As described further below, the beam produced through a SONG (Strachan-Ovokaitys Node Generator) device will have much deeper depth of penetration with intact modulation. This can thus allow the directed migration and adherence of stem cells with the particular intention of increasing the yield of stem cells delivered to a target tissue in need of regeneration or repair.

The present specification is directed toward methods of repairing, regenerating, curing, or treating damaged biological tissue, such as lung tissue, kidney tissue, blood vessels, immune system cells, cardiac tissue, cartilage tissue, bone tissue, teeth, liver tissue, endocrine tissues, pituitary tissue, thymus tissue, intervertebral discs, brain tissue, spinal tissue, or nerve tissue by obtaining unactivated stem cells, forming activated stem cells from the unactivated stem cells by treating the unactivated stem cells with an amplitude modulated laser beam having a pre-defined wavelength and a pre-defined amplitude, and administering the activated stem cells into a body containing the biological tissue.

The method may further comprise using a homing beam to guide the activated stem cells within the body to the location of the biological tissue. Optionally, the pre-defined wavelength is in a range of 405 to 980 nanometers. Optionally, the pre-defined frequency is in a range of 8 to 12 MHz. Optionally, prior to treating the unactivated stem cells, the laser beam is expanded in a range of two to ten times by passing the laser beam through a beam expander. Optionally, prior to treating the unactivated stem cells, the laser beam is passed through a Strachan-Ovokaitys Node Generator. Optionally, a phase cancellation of the laser beam is adjusted to achieve a predetermined power output before treating the unactivated stem cells.

Optionally, treating the unactivated stem cells comprises applying the amplitude modulated laser beam having a wavelength lying in a range of 405 to 980 nanometers to a container containing the unactivated stem cells, wherein the container is rotated at a speed of one complete rotation every 3 to 5 seconds and wherein the container is moved up and down for approximately 15 seconds in each direction simultaneous to the rotation. Optionally, the laser beam has a wavelength of 674 nm. Optionally, the unactivated stem cells are autologous or exogenous. Optionally, relative to the unactivated stem cells, the activated stem cells comprise at least one of an increased expression of an alpha or beta integrin, an increase in CD34, or an enhanced migratory action in a direction of the homing beam. Optionally, the frequency of the laser beam is modulated within a range of 8 to 12 MHz. In an embodiment, a phase cancellation of the laser beam is adjusted to achieve a predetermined power output before treating the unactivated stem cells.

Optionally, the exogenous unactivated stem cells are sourced from placenta and/or cord blood.

The present specification is also directed toward systems for repairing, regenerating, curing, or treating damaged biological tissue, such as lung tissue, kidney tissue, blood vessels, immune system cells, cardiac tissue, cartilage tissue, bone tissue, teeth, liver tissue, endocrine tissues, pituitary tissue, thymus tissue, intervertebral discs, brain tissue, spinal tissue, or nerve tissue. The system comprises an amplitude modulator for generating an amplitude modulated laser beam, a beam expander for expanding the amplitude modulated laser beam, a phase cancellation device for adjusting a phase cancellation of the laser beam to obtain a predetermined power output of the laser beam, a container adapted to contain stem cells, wherein the laser beam is configured to be directed toward the container for a predetermined period of time in order to form activated stem cells, and a homing beam adapted to be directed toward said damaged biological tissue and configured to guide the activated stem cells toward said damaged biological tissue.

Optionally, the system further comprises a Strachan-Ovokaitys Node Generator to obtain a predetermined wavelength of the laser beam. Optionally, the amplitude modulated laser beam has a wavelength lying in a range of 405 to 980 nanometers. Optionally, the amplitude modulated laser beam is modulated to have a frequency within a range of 8 to 12 MHz. Optionally, the amplitude modulated laser beam is configured to be passed through the beam expander in order to expand the amplitude modulated laser beam in a range of 2 to 10 times. Optionally, the container is adapted to be rotated at a speed of one rotation every 3 to 5 seconds and simultaneously moved up and down for approximately 15 seconds. Optionally, after exposure to said amplitude modulated laser beam, the activated stem cells comprise at least one of an increased expression of an alpha or beta integrin, an increase in CD34, or an enhanced migratory action in a direction of the homing beam compared to the stem cells prior to exposure to said amplitude modulated laser beam.

The present application discloses a method of repairing damaged biological tissue comprising obtaining unactivated stem cells, forming activated stem cells from the unactivated stem cells by treating the stem cells with an amplitude modulated laser beam having a pre-defined wavelength and a pre-defined amplitude, administering the activated stem cells into a body containing the biological tissue, and transcutaneously applying a homing coherent laser beam along at least one axis such that the homing coherent laser beam interacts with said damaged biological tissue.

Optionally, the homing coherent laser beam is generated using a 20% to 90% phase cancellation. The unactivated stem cells are harvested from an autologous source including at least one of peripheral blood, bone marrow, fat, or dental pulp. The unactivated stem cells are harvested from an exogenous source including at least one of a cord blood or a placenta of the patient. The unactivated stem cells may also be sourced from a genetically matched stem cell donor. The pre-defined wavelength is in a range of 405 to 980 nanometers. The laser beam has a wavelength of 674 nanometers. The laser beam comprises a string of short duration pulses of sub-femto second duration. Prior to treating the unactivated stem cells, the laser beam is expanded in a range varying between two times to ten times by passing the laser beam through a beam expander. Prior to treating the unactivated stem cells, the laser beam is passed through a Strachan-Ovokaitys Node Generator and a phase cancellation of the laser beam is adjusted to achieve a predetermined power output before treating the unactivated stem cells. Optionally, treating the unactivated stem cells comprises applying the amplitude modulated laser beam to a container containing the unactivated stem cells such that the container is rotated and simultaneously moved up and down in a vertical direction during the activation process. The container is rotated at a speed of one rotation in every 3 to 5 seconds and is moved up and down for a duration of 15 seconds in each direction. Relative to the unactivated stem cells, the activated stem cells comprise at least one of an increased expression of an alpha or beta integrin, an increase in CD34, or an enhanced migratory action in a direction of the homing coherent laser beam. The biological tissue is at least one of myocardial tissue, lung tissue, kidney tissue, blood vessels, immune system cells, cardiac tissue, cartilage tissue, bone tissue, teeth, liver tissue, endocrine tissues, pituitary tissue, thymus tissue, intervertebral discs, brain tissue, spinal tissue, pancreatic tissue and nerve tissue. Optionally, the unactivated stem cells are dormant cells that are in blood and separated out.

The present application discloses a method of treating damaged cardiac tissue of a patient comprising obtaining unactivated stem cells, forming activated stem cells from the unactivated stem cells by treating the stem cells with an amplitude modulated laser beam having a pre-defined wavelength and a pre-defined amplitude, intravenously administering the activated stem cells into the patient, and transcutaneously applying a homing laser beam along at least one axis such that the homing laser beam interacts with said cardiac tissue. The homing laser beam is generated using a 20% to 90% phase cancellation.

The present application discloses a method of treating a neurological condition in a patient comprising obtaining unactivated stem cells, forming activated stem cells from the unactivated stem cells by treating the stem cells with an amplitude modulated laser beam having a pre-defined wavelength and a pre-defined amplitude, intravenously administering the activated stem cells into the patient, and transcutaneously applying a homing coherent laser beam along at least one axis such that the homing coherent laser beam interacts with brain tissue and/or spinal cord tissue of the patient. Optionally, the homing coherent laser beam is swept over said spine cord tissue and swept over said brain tissue. Optionally, the homing coherent laser beam is generated using a 20% to 90% phase cancellation.

The aforementioned and other embodiments of the present shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein:

FIG. 6 illustrates a table showing the ejection fraction value for patients participating in a clinical trial at various time intervals during the ninety day period post stem cell implantation for the treatment of an end stage heart failure condition;

FIG. 8 illustrates a graph showing the net change in ejection fraction value for patients participating in a clinical trial ninety days after the treatment.

DETAILED DESCRIPTION

Figure 1:
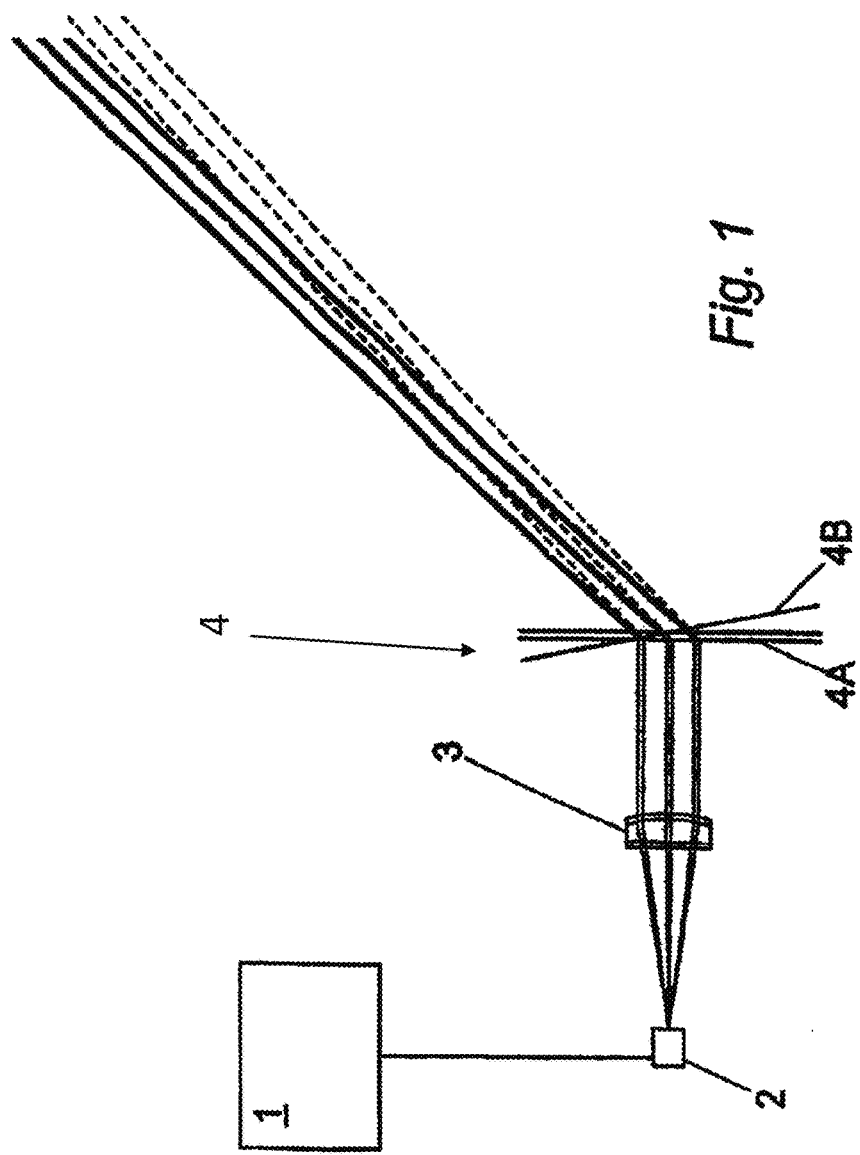
FIG. 1 illustrates a Strachan-Ovokaitys Node Generator device as disclosed in U.S. Pat. No. 6,811,564, which is incorporated herein by reference in its entirety.

The present specification is directed towards a composition of activated stem cells obtained by processing unactivated stem cells. In an embodiment, the methods and systems described in the present specification involve applying amplitude modulated pulses of laser light to unactivated stem cells to create said activated stem cells. In various embodiments, a stem cell may be defined as an undifferentiated cell of a multi-cellular organism that is capable of giving rise to substantially more cells of the same type, and from which certain other kinds of cell can arise by differentiation.

Stem cells have the ability to divide and create an identical copy of themselves through a process called "self-renewal". Stem cells can also divide to form cells that mature into cells that make up every type of tissue and organ in the body. In theory, a large enough dose of robust stem cells could repair any damaged or degenerated tissue completely. However, in practice, the application of stem cells at the desired tissue in the human body in not easy. There are strong challenges associated with transporting the cells to the desired location, having them stay at the desired location and achieving the repair at the desired location. Failure to achieve these objectives has limited the utility of stem cell therapy thus far, resulting in results that are largely equivocal.

Laser based stem cell therapy has shown promising results. The use of a laser beam helps to quickly and intensely attract the cells to the beam location and it also increases cell adhesion such that the cells remain at the desired location rather than passing through. Cell adhesion is the basis of cell-to-cell communication that allows the local tissue to direct the desired repair.

Typical stem cell therapy may require three to six weeks to observe results, which may be limited or statistically insignificant. In contrast, the laser activated and guided stem cells therapy disclosed in the present specification has resulted in clinical improvement in less than twenty four hours. Further, the degree of symptomatic and objective recovery is much greater than other methods.

In embodiments, the present specification describes a unique laser guidance platform that involves pre-activation of the stem cells to enhance their adhesion characteristics and subsequent application of such cells to the desired tissues through use of a deeply penetrating low energy laser beam.

In an embodiment of the present specification, unactivated stem cells are autologous or exogenous. The pulses of laser light have a wavelength in a range of 300 nm to 1000 nm, and, in an embodiment, approximately 674 nm. In an embodiment, the pulses of laser light are passed through a beam expander and are phase conjugated before being applied to the unactivated stem cells.

In various embodiments, an activated stem cell is one that, relative to the original stem cell, has at least one of the following improved traits: an increased cell surface expression of an alpha or beta integrin, more specifically alpha 4, beta 1 or beta 2 integrin, an increase in CD34, or an enhanced migratory action in the direction of the applied beam.

In another embodiment, the present specification discloses a method of treating a patient with an area of tissue in need of regeneration, reconstitution, or repair comprising administering to the patient a composition comprising the activated stem cells and, using a laser beam, guiding the activated stem cells to said area of tissue. In embodiments, the laser beam comprises amplitude modulated pulses of laser light and causes a three dimensional directional localization of said activated stem cells. The adherence of activated stem cells to a target tissue is higher relative to an adherence of unactivated stem cells. In an embodiment, the method of treating results in reversing neurologic deficits arising from cerebral palsy in a patient. In another embodiment, the method of treating results in regenerating myocardial tissue and improving cardiac function in another patient. In yet another embodiment, the method of treating results in repairing a spinal cord injury in a patient.

The various embodiments of the present specification are based on experiments that involve applying an amplitude modulated laser beam through a flask of cells. The general observation in the above experiments was that the cells had lined up in the form of a string comprising multiple cells adhering to each other in the area where the beam had been applied. In an embodiment, a primitive cell line Kg1a, which has stem cell like features, was found to have increased its expression of the hematopoietic stem cell marker CD34. Upon further review it was also realized that the nature of the modulated laser signal would be broadly stimulating to the cell adhesion and communication molecules known as alpha and beta integrins. Flow cytometry showed a variable yet significant increase in the measurement of beta 1, beta 2 and alpha 4 integrin molecules on the cell surface that peaked in 24 hours and declined after 48 hours. Visible observations depicted that the cell to cell and cell to surface (of the flask) adhesion were markedly increased wherever the beam was directed in a flask of cells. A stimulus that will increase migration and localization of stem cells, while also increasing cell adhesion molecule expression in stem cells, as well as tissue stimulated with such a resonant signal, would tend to draw stem cells to where the beam is directed and favor their remaining in the tissue, also thus stimulated to be more adherent.

In one embodiment, the stem cells, which are activated in accordance with the methods disclosed herein, have an increased degree of cell adhesion as compared to stem cells which are not activated. In one embodiment, the stem cells, which are activated in accordance with the methods disclosed herein, have an increased degree of expression of CD34 as compared to stem cells which are not activated. In one embodiment, the stem cells, which are activated in accordance with the methods disclosed herein, have an increased degree of expression of integrin molecules as compared to stem cells which are not activated.

As described further below, the beam produced through a SONG device tends to have a much deeper depth of penetration with intact modulation. This allows the directed migration and adherence of stem cells with the particular intention of increasing the yield of stem cells delivered to a target tissue in need of regeneration or repair. It should be appreciated that the present invention achieves markedly improved therapeutic results relative to the prior art because the radiation used in the present invention achieves a far greater penetration depth than previously disclosed radiation-based stem cell guidance or homing methods. Specifically, prior art radiation-based stem cell guidance or homing methods use light that can only penetrate, at most, 5 mm below the patient's epidermal surface. In contrast, the light source used in the present invention can penetrate deep inside the body and therefore make contact with any and every internal organ, thereby enabling the guidance of any intravenously introduced group of activated stem cells to any organ, including the stomach, small intestine, large intestine, rectum, anus, lungs, nose, bronchi, kidneys, urinary bladder, urethra, pituitary gland, adrenal, thyroid, pancreas, parathyroid, prostate glands, heart, blood vessels, spleen, uterus, testis, ovaries, mammary glands, brain and spinal cord. In one embodiment, each of the disclosed treatments has a homing step in which the radiation source, described below, is positioned external to the patient such that the emitted radiation has the shortest, most direct pathway through the body and to the target tissue.

The systems and the methods disclosed in the present specification are used to treat every organ of the human body by using activated stem cells. By directing such stem cells towards any tissue or organ the regeneration and repair of the tissue or organ is accelerated many fold. In various embodiments, the system and methods disclosed herein are used to rebuild lungs, kidneys, blood vessels, immune system, bones, teeth, liver, endocrine tissues such as thyroid and pancreas, pituitary and thymus, intervertebral discs, among other tissues and organs. Treatment of exemplary patient conditions, using embodiments disclosed herein, have:

Treated congestive heart failure. Patients with severe end stage disease (cardiac ejection fractions in the 15% range) have shown benefit within the day of treatment. Over a period of 3 to 6 weeks that involved 2 to 3 treatment sessions, 50-100% or greater relative increases in cardiac ejection fraction have been seen. Remarkable improvements in clinical condition and relief of symptoms have been observed in patients treated using systems and methods of the present specification.

Treated Parkinson's disease. Treated patients have exhibited reduced tremors, decreased rigidity and longer walking strides with greater stability. Speech, breathing, and coordination have also been significantly improved.

Treated Multiple Sclerosis, with significant success when the cells are guided to the areas of localized neural injury. One subject who was in an acute exacerbation phase showed improved arm and leg strength, better speech, and enhanced coordination within an hour of the treatment.

Treated spinal injury. Treated patients have shown improved arm and leg function and sensation below the mid-cervical lesion evolving over 6-8 weeks after the treatment.

Treated cerebral palsy. Treated patients have shown reduced spasticity, increased range of motion, and improved fine motor coordination. A single treatment can bring new functional capacity, even for patients in which standing and walking has not been present.

Treated amyotrophic lateral sclerosis (ALS, or Lou Gehrig's Disease). Protocols have shown a remarkable recovery in a rapidly progressive bulbar case (presents with speech and swallowing as opposed to these being late phase). Within one hour of the treatment, a patient had greater strength in her arms and legs, along with improved speech, swallowing and lingual coordination. Eight weeks post treatment, instead of the expected return to progression, the patient continued to be in a significantly improved and stable state.

Treated knee injuries. Treated patients have shown rapid healing in knee cartilage tears, specifically in the menisci, and have even been able to regenerate cartilage in bone on bone situations.

Provide anti-aging treatments. Patients who have received the laser activated stem cell treatment, given for rejuvenation purposes, have shown improved function and youthfulness.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

It should be noted herein that any feature or component described in association with a specific embodiment may be used and implemented with any other embodiment unless clearly indicated otherwise.

In various embodiments, for activation, the stem cells are treated with a laser process including exposing them to a predefined laser wavelength at a predefined amplitude modulation that is passed through a beam expander such as Strachan-Ovokaitys Node Generator or SONG device, which is disclosed in U.S. Pat. No. 6,811,564 and incorporated herein by reference.

FIG. 1 illustrates a SONG device as disclosed in U.S. Pat. No. 6,811,564. Referring to FIG. 1, the SONG device comprises a laser diode 2 which is controlled by an amplitude modulator 1. The laser diode 2 is selected to have a substantially linear relationship between current and wavelength with minimum mode hopping. The amplitude modulator 1 modulates the current to the laser diode 2 which, in turn, results in a very small wavelength modulation of the laser, for purposes discussed below.

Figure 2:
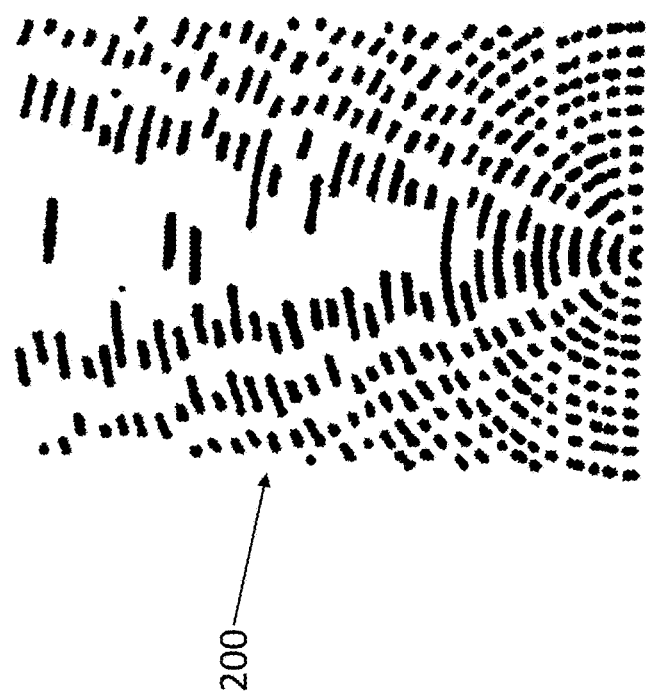
FIG. 2 shows the sparse constructive interference effect from a 1 percent bandwidth cancellation plate having a 5 mm aperture.

The output of the laser diode 2 is collimated by a lens 3 and passed to an optical element 4. The optical element 4 consists of a first diffraction grating, a refractive element, and a second diffraction grating such that the beam is substantially cancelled. This allows the cancellation to occur over a small percentage of the wavelength variance of the laser source, rather than at a single critical wavelength. Wavelengths beyond the acceptance bandwidth of the cancelling optic 4 above and below the center frequency pass without being cancelled. This means that a complex Fresnel/Fraunhoffer zone is generated, defined by the beat frequency of the high and low frequencies as a function of the aperture. Consequently, relatively sparse zones of constructive interference occur between the high and low frequency passes of the cancellation element in selected directions from the aperture, as shown in FIG. 2. FIG. 2 shows the sparse constructive interference effect from a 1 percent bandwidth cancellation plate of 5 mm aperture. Black represents constructive nodes.

As seen in FIG. 1, the optical element 4 can be adjusted angularly between positions 4A and 4B. This varies the ratio of constructive to destructive interference.

In effect, the continuous beam is transformed into a string of extremely short duration pulses typically of sub femto second duration. The small wavelength modulation of the laser diode 2 causes the constructive and destructive nodes to move rapidly through the volume of the Fresnel zone of the collimator lens aperture. This has the effect of stimulating very short (sub picosecond) pulse behavior at any point in the Fresnel zone through which the nodes pass at a pulse repetition frequency defined by the amplitude modulator frequency.

The wavelength of the cancellation and constructive interference zones for a theoretical single path would be the difference between the two frequencies. If the bandwidth of the cancelling element is narrow, this difference is very small and the effective wavelength of the cancelled/non-cancelled cycle would be very long, on the order of picoseconds. Therefore, the system would behave substantially similarly to a system with no cancellation because it requires an aperture much larger than the primary light wavelength to generate a useful Fresnel/Fraunhoffer zone. Such an aperture would greatly multiply the available Feynman diagram paths eliminating any useful effect, even if it were possible to generate a sufficiently coherent source of such an aperture.

If the beat frequency can be made high enough, the wavelength of the cancelled to non-cancelled cycle can be a fraction of a practical aperture. This will make this wavelength sufficiently small to limit the Feynman paths to within a cycle or two in free space allowing the Fresnel/Fraunhoffer effect to be apparent. Since the center frequency and spectrum spread of a laser diode is modulated by adjusting the current and or temperature of the junction, the pattern of the Fresnel/Fraunhoffer zones is varied substantially by very small variations in the wavelength of one or both pass frequencies. Such modulation is produced in the apparatus of FIG. 1 by the amplitude modulator 2.

A conventional coherent or incoherent beam would have high probability paths in the Feynman diagram. These paths would overlap at very low frequencies (kHz) and be of little practical use in the stimulation of molecular resonance. It should be noted however that the phenomena described above is used as a means to multiply the modulation frequency, up to the point where the beam effectively becomes continuous. Thus, by properly selecting the aperture, the region of the beam selected for transmission through the medium, and the modulation frequency, it is possible to cause the constructive nodes to pass across any given point in the beam at frequencies many times higher than the modulation frequency. In ideal conditions, the duration of exposure to a constructive node of any point would be for a period equivalent to a quarter of the duration of a wavelength of the molecular frequency repeated once per cycle.

If the wavelength of the laser is chosen to be one easily absorbed by the atomic structures it is desired to induce to resonance, then the beam will efficiently deliver the desired modulation frequency to the desired molecules. Cell adhesion molecules and human integrins such as alpha 4 and beta 1 are ideally suited for excitation to chemical activity by this method.

The sources of cells for the procedure described herein may be autologous or exogenous. Autologous stem cells refer to cells which are derived from the same person who is to be treated with such cells. These cells will be a genetic match obviating risks of rejection of cells. In current methods, autologous stem cells are either derived or concentrated from peripheral blood, bone marrow or fat, yet other tissues could be a source of autologous stem cells as virtually every tissue of the body has its own distinct stem cell reservoir.

A preferred exogenous source of stem cells is umbilical cord blood. Stem cells from cord blood are very robust with long telomeres (a genetic aging clock level of newborn level) and a strong capacity for tissue repair. Functionally, rejection syndromes of the cells and graft versus host disease (GVHD) have not been issues with this source of cells in the context of an intact immune system. Matched bone marrow could also be a source of cells, though a high degree of matching would be required to avoid rejection and GVHD. In practice, for regeneration as opposed to anti-leukemic medical regimes, cord blood stem cells have been used safely.

In an embodiment of the present specification the exogenous stem cells used in the treatment are sourced from both cord blood cells and placenta. In an embodiment of the present specification used in a government approved clinical trial, the stem cells sourced from cord blood cells and placenta from a single delivery were used for treatment of end stage heart failure condition and the results obtained are extremely encouraging.

Figure 3:
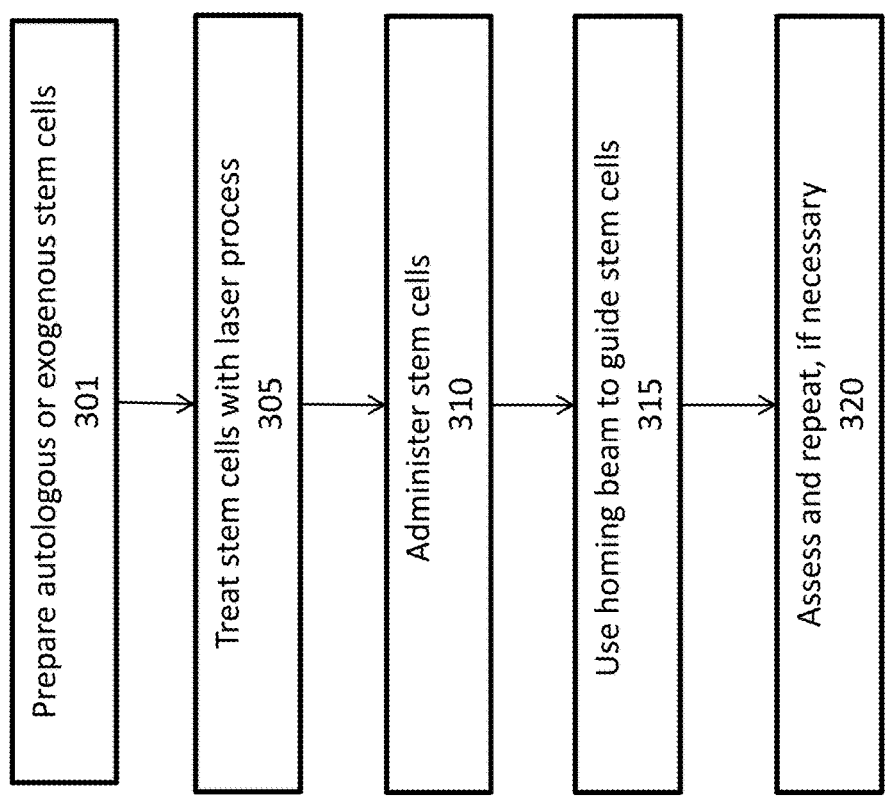
FIG. 3 is a flowchart illustrating a method of activating stem cells and using them to treat a tissue requiring treatment, in accordance with an embodiment of the present specification.

FIG. 3 is a flowchart illustrating a method of activating stem cells and using them to treat a tissue requiring treatment, in accordance with an embodiment of the present specification. Referring to FIG. 3, autologous or exogenous stem cells to be administered are pre-treated with ultra-rapid impulses of modulated laser light before administration to a patient. The general procedure comprises first preparing cells for treatment (step 301) by isolating autologous or exogenous stem cells in a biologically compatible solution. The stem cells are then treated with a laser process (step 305), including exposing them to a predefined laser wavelength at a predefined amplitude modulation that is passed through a beam expander Strachan-Ovokaitys Node Generator, as further described in the examples below.

The now activated stem cells are administered to a patient (step 310), usually by IV infusion, although other routes such as intranasal, intra-CSF, and selective intra-articular or intra-arterial injection are also possible. The stem cells are guided to the target treatment location (step 315) by directing a homing beam transcutaneously to the target tissue from two or more axes that intersect in the desired target volume. The patient's clinical response is assessed and the procedure is repeated (step 320), if necessary, until the optimal or desired results are achieved.

The homing beam, or guiding signal, is preferably a laser beam that is directed, transcutaneously, over the surface of the entire volume of the organ or tissue to be treated, from at least one and preferably two to three axes. Accordingly, a patient is positioned on a table and positioned such that the externally positioned laser beam has the most direct pathway to the target tissue along a first axis and such that the laser beam can be moved to a second and/or third position to have direct pathways to the target tissue along a second and third axis, wherein the second and third axis point along different directions relative to each other and relative to the first axis. A coherent laser beam is then generated using a 20-90% phase cancellation, preferably 50% to 70% phase cancellation and more preferably 60% phase cancellation. The coherent laser beam is further configured to target a specific anatomical location or to sweep over an anatomical location, depending on the size of area being treated. For example, the guiding or homing laser beam may sweep a larger organ at an approximate rate of 1 to 2 cms per second.

Figure 4:
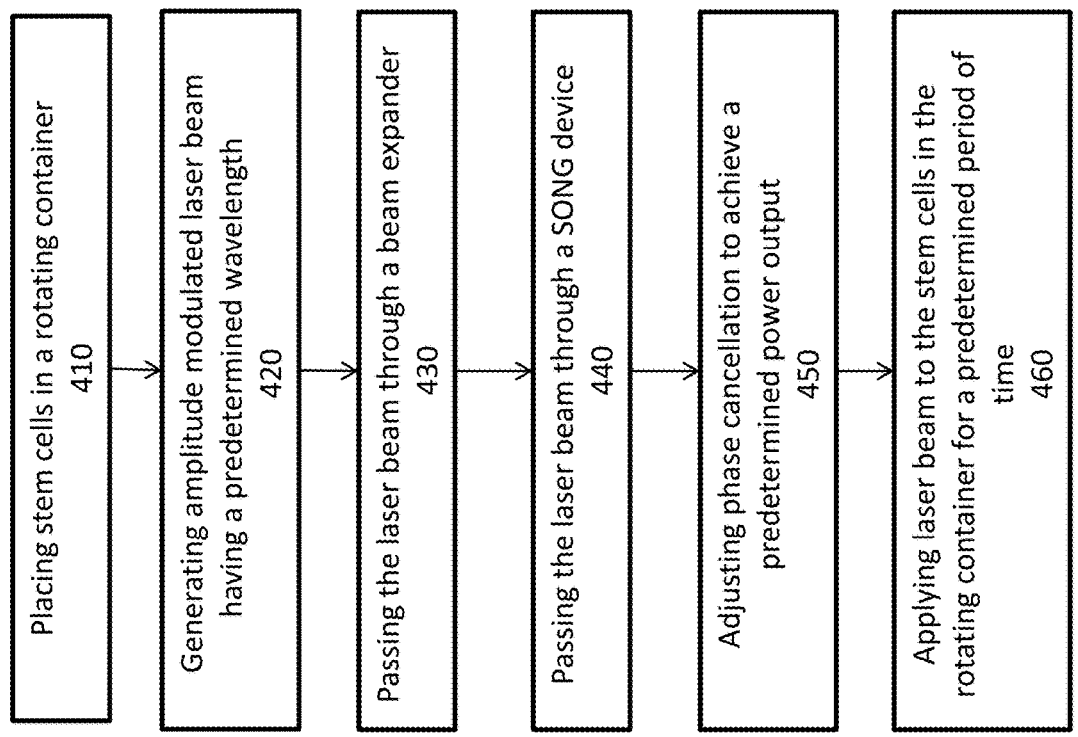
FIG. 4 illustrates the steps of activating stem cells by using a laser based process, in accordance with an embodiment of the present specification.

FIG. 4 illustrates the steps of activating stem cells by using a laser based process, in accordance with an embodiment of the present specification. In various embodiments, the steps of preparing autologous or exogenous stem cells and treating them with a laser process comprise placing the unactivated stem cells in a container which is capable of rotation (step 410). In an embodiment, the speed of rotation of the container is approximately one rotation per 3 to 5 seconds. In an embodiment, the container also moves in a plane perpendicular to the plane of rotation. The container moves in an upward and downward direction with respect to the plane of rotation for a duration of about 15 seconds in each direction. In an embodiment, the height of the container is a multiple of the height of a laser beam that is used to treat the unactivated stem cells.

Next at step 420, an amplitude modulated laser beam having a predetermined wavelength is generated. In various embodiments, the laser beam has a wavelength in the range of 405 to 980 nanometers (nm). In an embodiment, the laser beam has a wavelength of approximately 674 nm. In an embodiment, the frequency of the laser beam is modulated within a range of 8 to 12 MHz.

At step 430, the laser beam is passed through a beam expander for expanding the beam between two to ten times. In other embodiments, the laser beam is expanded less than two times or more than ten times. Next, at step 440 the laser beam is passed through a Strachan-Ovokaitys Node Generator (SONG) such as one explained with reference to FIGS. 1 and 2 above.

At step 450, phase cancellation is adjusted to achieve a required power output of the laser beam. The phase cancellation is adjusted by measuring the power output, adjusting the beam to minimum cancellation as defined by the measured power being at the maximum and then changing the angle until the desired percentage calculation is reached by the measured power reducing to this level.

At step 460 the laser beam is applied to the rotating container in order to activate the stem cells.

In an embodiment, the above described process results in stem cells that, relative to the administration of unactivated stem cells, have an increased cell surface expression of alpha 4, beta 1 and beta 2 integrins. In an embodiment, the above described process results in stem cells that, relative to the administration of unactivated stem cells, have an approximately 30-35% increase in CD34, the hematopoietic stem cell surface marker.

Figure 5:
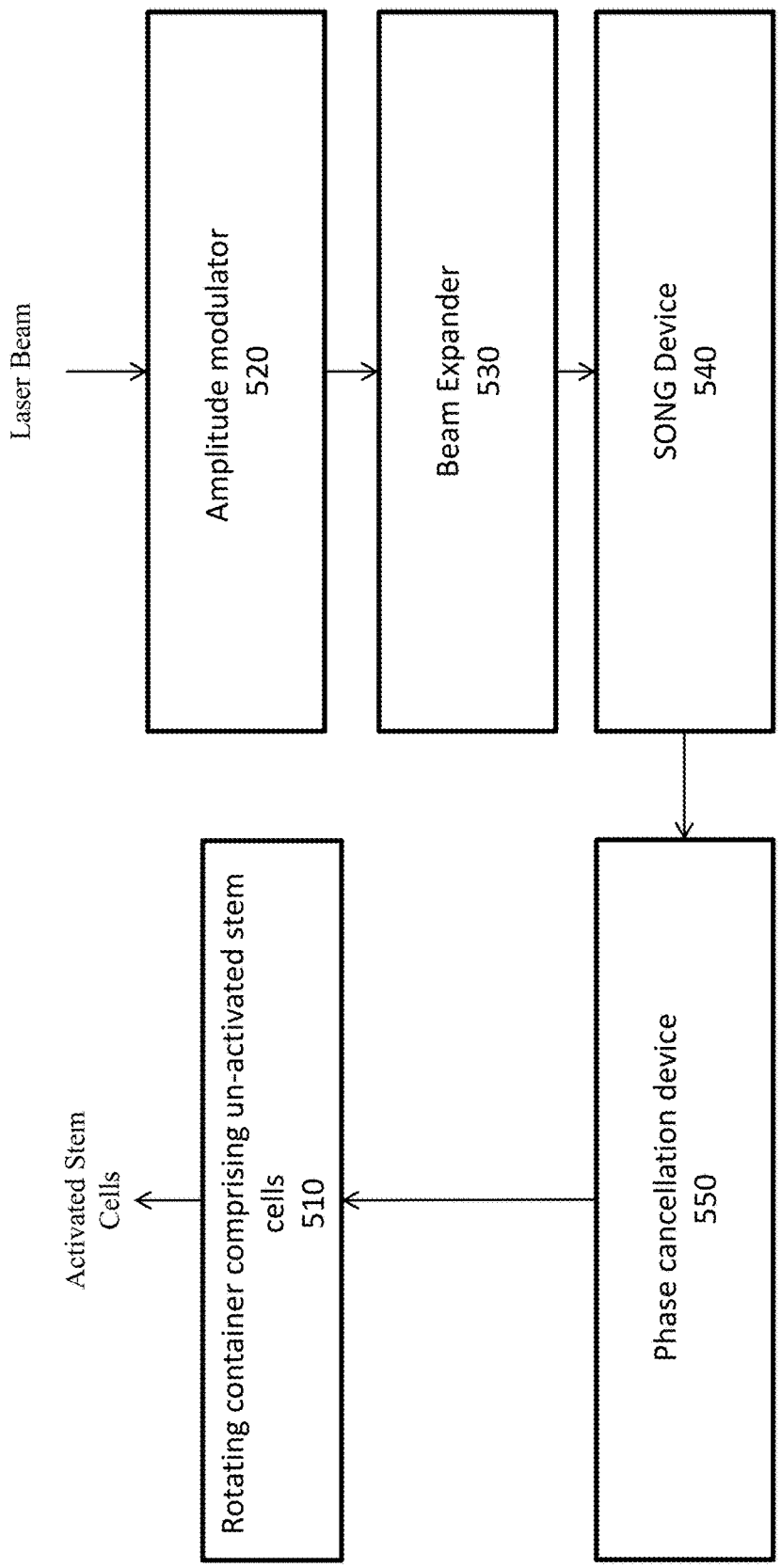
FIG. 5 is a block diagram illustrating a system for generation of activated stem cells by applying an amplitude modulated laser beam having a predetermined wavelength and power output to a container containing un-activated stem cells, in accordance with an embodiment of the present specification.

FIG. 5 is a block diagram illustrating a system for generation of activated stem cells by applying an amplitude modulated laser beam having a predetermined wavelength and power output to a container containing un-activated stem cells. System 500 comprises a rotating container 510 comprising un-activated stem cells, an amplitude modulator 520 for modulating a laser beam to obtain a laser beam having an amplitude modulated in the range of 405 to 980 nanometers, a beam expander 530 for expanding the laser beam between two and ten times, a Strachan-Ovokaitys Node Generator 540 as a phase cancellation device for adjusting a phase cancellation of the laser beam 550 to obtain a predetermined power output of the laser beam. In various embodiments, the container is rotated at a speed of one rotation every 3 to 5 seconds and/or is simultaneously moved up and down for approximately 15 seconds in each direction.

In embodiments, the systems and methods described in the present specification are able to create stem cells that have biologic potency of newborn cells. In embodiments, the unactivated stem cells are processed such that the positive particles in such cells are telomerased which on activation have telomeres as long as a newborn or possibly even longer. Further, the activated stem cells produced are free of any added growth factors or chemicals.

Typical stem cell based treatments require about one million cells per kg of body weight which means about 50-100 million cells for most adults. In embodiments, the procedure described in the present specification yield about one billion particles or stem cells that are highly activated. In embodiments involving advanced immuno-magnetic separation, about 10 billion particles can be generated.

Another significant advantage of the systems and methods described in the present specification relates to the size of the activated particles. Typical 10 micron size stem cells in autologous or allogenic treatments have a high probability of getting caught in lung capillaries if administered through intravenous means which means the actual systemic delivery is a small fraction of the dose. In embodiments of the present specification, tiny sized particles are generated which provide advantage in neurologic applications. In an embodiment, the 1-2 micron size of the activated particles allows easier passage through the lung and also through the blood brain barrier.

The laser activated and guided stem cell therapy disclosed in the present specification is very unique in two important ways. The first is the ability to stimulate dormant circulating repair cells that appear dead to become active and highly functional. The other is the creation of a laser-guidance signal that attracts cells to where the beam is directed in tissue, increases the cells' adhesiveness, and thereby supports their integration in the location to which they have been directed. Both of these properties set this work apart from all the other methods in this actively-evolving field. The stem cells thus awakened are an ideal match to the person from whom they were drawn, making them a safe and especially potent source of cells for regeneration.

An extraordinary property of the dormant repair particles is that they are telomerase positive. Telomerase is the enzyme that elongates the region at the ends of the chromosomes known as telomeres. When a person is born the telomeres are long. Each time the cells divide, little bits of the telomeres tend to chip off and they get shorter over time. The telomeres are likened to the plastic tips of shoe laces that are necessary to keep the shoestrings from unraveling and coming apart. When the telomeres get short the cells divide less often and organs and tissues regress in size and function. When the telomeres are too short, about half of their length at birth (and one third of their length at the time of conception), that is usually the limit of the human life span. Telomerase can lengthen the telomeres again and can literally turn back the aging clock. This enzyme is usually turned off which is why cells and tissues undergo aging. When the dormant cells are awakened they are alive with the vitality of activated telomerase with exceptionally long telomeres of one day old biology or even younger.

The greatest obstacle for stem cell therapy is usually getting cells to localize and adhere in the intended location to affect the desired repair. To treat heart failure, cardiac catheterization has been used to infuse the stem cells straight into the arteries of the heart. A summary of multiple published studies showed that this method increased heart function about 8% in 180 days. With laser-activated and laser-guided stem cells, in a comparative clinical trial, stem cells given by the minimally invasive IV route but with laser guidance showed an over 50% greater clinical effect about 60 times faster in only 3 days from one treatment. Laser guidance appeared to be much more effective to localize the cells than the more invasive method directly into the arteries. The degree of the effect was comparable to reversing the time course of the disease process by 5-15 years, in essence turning back the clock for the tissue.

Case Study 1: Laser Guided Stem Cells to Reverse Cerebral Palsy.

Patient: A 20 year old female with cerebral palsy due to hypoxic brain injury has had significant disabilities since infancy. While her cognition was fairly well preserved, she had marked spasticity and her knees had significant flexion restriction. Her speech was understandable and coherent yet breathy. Her examination was remarkable for an imbalance of conjugate gaze, with the right eye tending to drift outward. Other cranial nerve exam was fairly intact except for speech being mildly dysarthric. Her upper extremity strength was normal except for a weak grip and tone was relatively normal. In contrast, her lower extremities showed marked spasticity, with flexion to about 45 degrees at the knees, such that it was not possible to stand unassisted.

Procedure: 10 million umbilical cord blood stem cells were prepared for injection. These cells were concentrated into about 3 cc. They were treated before injection with a laser of wavelength 674 nm and an amplitude modulation at 10 MHz that first passed through a 5× beam expander and then through a Strachan-Ovokaitys Node Generator, or SONG device, which is described herein.

At minimum phase cancellation through the device, the power output was 1.15 mW, which was then phase cancelled by adjusting the optics to an output of 0.46 mW. The residual light is in the form of sparse nodes of constructive interference that have much greater depth of penetration than ordinary laser light in visible wavelengths which is intensely scattered beyond 2-5 mm. The cells were activated by slowly rotating the syringe containing the cells through the beam for 77 seconds.

The activated stem cells were administered to the patient by a slow IV push over a 3 minute period of time. Upon infusion of the activated stem cells, they were directed to the brain and spinal cord with a beam slowly scanning up and down the central spine or slowly scanning back and forth, then up and down over the respective regions of the brain until the entire area had been scanned. The rate of beam movement was approximately 1-2 cm per second over the respective areas projected transcutaneously as follows:

Lower spine: 2.5 minutes
Upper Spine: 2.5 minutes
Right Occipital: 1 minute
Right Temporo-Parietal: 3 minutes
Right Frontal: 1 minute
Left Frontal: 1 minute
Left Temporo-Parietal: 3 minutes
Left Occipital: 1 minute In various embodiments, cell adhesion molecules of the stem cells get activated by application of amplitude modulated laser beam as explained above. Further activation of the stem cells takes place when these cells are guided within a body to reach a target tissue by using the laser guidance process. In some embodiments, a photo-attraction effect from the guiding laser beam that could also be related to activation of the state of cell adhesion molecules takes place. The activity of cell adhesion molecules in the volume of tissue that the guiding laser beam stimulates makes both the stem cells and target tissue stickier. Hence, the stem cells have a greater tendency not only to stay where the guiding laser beam has been as they circulate through the body but to be instructed by the native tissue regarding the state the stem cells should attain and the manner in which they should integrate in the tissue.

In various embodiments, the area of coverage of the guiding laser beam is the area that allows directing the beam over the surface projection of the entire volume of the organ or tissue to be treated, from at least one and preferably two to three axes, the latter collimated to get the highest overall summated treatment to the desired volume of tissue. In an embodiment 20-90% phase cancellation of the guiding laser beam is carried out. In another embodiment the phase cancellation of the laser beam is within 50% to 70%. In yet another embodiment, approximately 60% phase cancellation is carried out. In various embodiments, the guiding laser beam may stay at the location of the tissue requiring treatment for the entire time of the treatment when the area requiring treatment is small as in Parkinson's disease, or may sweep a larger organ at an approximate rate of 1 to 2 cms per second.

Results: The procedure was well tolerated. Immediately afterwards she described feeling energy and tingling in her brain and body, especially in her lower legs and feet. She also felt that there was already a reduction in spastic muscle tone, and she felt calm and relaxed.

Over one week she noted a remarkable increase in lower extremity flexibility and could extend her legs to within 10-12 degrees of straight. One month later she was able to stand without assistance. Remarkably, seven weeks after the procedure she was able to walk for short distances without assistance. She also observed a significant improvement in the fine coordination of her hands and fingers, enabling her to be able to draw rectangles and triangles for the first time. Her breathing control was improved, and she noted that she could talk and be understood on a phone much better than before.

Case Study 2: Laser Guided Stem Cells to Regenerate Myocardial Tissue and Function Patient: A 69 year old white male had end stage congestive cardiomyopathy with post multiple myocardial infarctions and a measured cardiac ejection fraction in the 15-17% range. His prognosis was very poor and was only given hope of sustained survival if he had an implantation of a left ventricular assist device. He was pale and cyanotic in appearance and communication was confused, consistent with a low perfusion state.

Procedure: 120 cc of peripheral blood were removed by vein from the subject. This was concentrated into 20 cc of stem cell rich plasma using a standard device for this procedure. This provided an estimated 10 million autologous blood derived stem cells and potentially another billion stem cells activated from the dormant population of circulating stem cells.

The cells were ozonated with 15 cc of ozone, which was bubbled through the cells. The laser configuration was 674 nm modulated at 10 MHz, passed through a 5× beam expander and then phase conjugated through a SONG device from 1.80 to 0.69 mW. The stem cells were treated in the syringe with this beam for 3 minutes.

The now activated stem cells were infused into the patient by a slow IV push over a 5 minute period. Upon infusion of the activated stem cells, they were directed to the heart with a beam directed transcutaneously to the myocardium via the anterior myocardial projection from the anterior chest wall for 5 minutes and the lateral myocardial projection via the lateral chest wall for 5 minutes. The beam was directed over these respective regions in slow sweeps side to side and up and down to cover the entire myocardial region in both of these axes, with the rate about 1-2 cm per second.

Results: The procedure was well tolerated. Fifteen to twenty minutes later the patient's skin had more color and his cyanotic lips turned pink and vibrant. His confused state of mind was much clearer. By 45-60 minutes, he had increased physical energy, got out his chair and danced to music playing in the office.

This procedure was repeated twice more at approximately 3 week intervals, with the patient showing increasing recovery of strength and function. The patient was able to enhance his ability to perform physical activity such as from being able to walk only a half block, which caused dyspnea due to exertion, to being able to walk several blocks and return to work. Follow-up echocardiogram after the third procedure showed a highly remarkable doubling of function to a 30-34% cardiac ejection fraction.

Case Study 3: Laser Guided Stem Cell Therapy to Repair Spinal Injury

Patient: A 24 year old male with quadriplegia four years after a C4-C5 fracture in a surfing accident had essentially no leg function and limited upper extremity proximal shrugging. He had a sensory level with markedly reduced sensation below the nipple line.

Procedure: Twenty million cord blood stem cells were prepared and were concentrated into about 5 cc. The laser configuration was 674 nm modulated at 10 MHz, passed through a 5× beam expander, and then phase conjugated with a SONG device from 0.85 mW to 0.33 mW. The cells were slowly rotated through the beam up and down for about 3 minutes. Five million of the cells were applied intranasally after the nasal passage had been prepped with hyaluronidase to enhance their ability to traverse the cribriform plate.

Fifteen million activated cord blood stem cells were infused into the patient by a slow IV push over a 5 minute time period. Upon infusion of the activated stem cells, they were directed to the treatment region by a laser beam which was applied transcutaneously over the C2-C8 area, sweeping vertically in slow movements over the central spine and then horizontally side to side 2.5 cm on either side of midline for 15 minutes duration.

Results: The procedure was well tolerated, though he had no particular subjective sensation of experience during the process itself. One week later, his sister (his primary caretaker) reported that he had more sensation in his abdominal region. He also had more physical energy and felt he could start to use light weights for his arms. Six to eight weeks later there was even more remarkable recovery, with extensive movement of his arms, including the ability to hit a tennis ball back with both palms. Some distal control was also possible with the ability to start feeding himself with some mechanical support. Using a Lokomat to mimic walking movements, he had improved to being able to support about 30% of his weight and could make kicking movements with his legs in a pool.

Case Study 4: Laser Guided Stem Cell Therapy to Restore Function in Multiple Sclerosis (MS)

Patient: A 52 year old white female with history of MS for 8 years presented with an exacerbation of neurologic symptoms. Primarily, she noted weakness in her left arm and left leg and problems with her speech and swallowing, which was confirmed on exam.

Procedure: 30 ml of fat from her medial thigh areas was harvested and then processed to yield a concentrate of adipose tissue derived mesenchymal stem cells. Approximately 60 ml of peripheral blood was removed and processed to concentrate stem cells, much as in Example 2. These cells were both then mixed into a bag of about 150 ml of 5% dextrose half normal saline.

The laser configuration was 674 nm modulated at 10 MHz, passed through a 5× beam expander, and then phase conjugated through a SONG device from 1.40 to 0.55 mW. The stem cells were treated in the IV bag with this beam moving slowly across and side to side for 5 minutes. The combination of adipose and peripheral blood derived stem cells were then infused intravenously over 95 minutes.

Upon infusion of the activated stem cells, they were directed to the brain and spinal cord with a beam slowly scanning up and down the central spine and/or by scanning back and forth, then up and down over the respective regions of the brain until the entire area had been scanned. The rate of beam movement was approximately 1-2 cm per second over the respective areas projected transcutaneously with the laser guidance step being done both at the beginning of the infusion and again after all the cells had been infused. The first of these began 35 minutes after the start of the infusion and the second immediately at the completion of the infusion 95 minutes after it had begun. Each of these two sessions had the following pattern and respective durations:

Right Occipital: 1 minute
Right Temporo-Parietal: 3 minutes
Right Frontal: 1 minute
Left Frontal: 1 minute
Left Temporo-Parietal: 3 minutes
Left Occipital: 1 minute
Spine: 5 minutes During the first of the laser applications, the patient described significant tingling and electrical sensations throughout her face and neck and then in her upper and lower back. During the second application, she felt significant tingling through her face, neck, and speech apparatus. She felt warmth and tingling strongly when the beam was between her shoulder blades, then up and down the spine with the beam.

Results: Twenty minutes after the completion of the procedure, her strength was markedly better in her left arm, with 3/5 (three on a scale of five) strength of proximal flexor and extensor muscles improved to 4.5/5 (four point five on a scale of five) strength. The strength of her left leg proximally and distally showed an essentially full recovery from 3.5/5 (three point five on a scale of five) to 5/5 (five on a scale of five) strength. After over one year of follow up, the improvement has persisted and she has been free of exacerbations of her disease.

Case Study 5: Laser Guided Stem Cell Therapy to Reverse Parkinson's Disease

Patient: 71 year old white male diagnosed with Parkinson's 12 years before and had gradual progression of disease. The patient was on drugs such as Mirapex, Stolevo, and Aspirin. He complained of soft speech, writing with small letters, shuffling gait, difficulty turning, and a tremor of his hands. His neurologic exam was remarkable for modest hearing loss of his right ear, motor function showing mild reduction of strength of flexing his lower legs bilaterally, finger to nose testing with a tendency to miss due to intention tremor, slow alternate finger touches, and a broad based gait with small steps that was slow with almost no arm swing, and heel to toe walking that was unstable.

Procedure: 30 ml of fat from the medial thigh areas was harvested and then processed to yield a concentrate of adipose tissue derived mesenchymal stem cells. About 60 ml of peripheral blood was removed and processed to concentrate stem cells, much as in Example 2. These cells were both then mixed into a bag of about 150 ml of 5% dextrose half normal saline.

The laser configuration was 674 nm modulated at 10 MHz, passed through a 5× beam expander, and then phase conjugated through a SONG device from 1.36 to 0.52 mW. The stem cells were treated in the IV bag with this beam moving slowly across and side to side for 5 minutes. The combination of adipose and peripheral blood derived stem cells were then infused slowly intravenously over 84 minutes.

After about 25 minutes after the infusion had begun, the homing laser was applied to the skin from the left lateral cranium perpendicular to the skin and targeting the substantia nigra for 3 minutes. The beam was then repositioned at about a 45 degree angle with respect to the axis of the first beam to approach the substantia nigra from 2 different axes, also for 3 minutes. This was repeated from the right side for 2 applications of 3 minutes each. Upon the infusion being completed this procedure was repeated for 2 applications of 3 minutes each on the right and left side. The procedure was well tolerated.

Results: Immediately following the completion of the protocol above, the neurologic exam was repeated and showed several improvements. Finger to nose testing was faster and more accurate with much reduced tremor. Alternate finger touching was faster and more accurate. His stride was longer and more balanced with improved arm swing. Heel to toe walking was better with more stability. Particularly striking, his speech was stronger and more resonant.

He had ups and downs after the procedure yet remained generally improved. He increased his work capacity from 2 to 3 clients daily. He had repetition of the procedure above 1 and 3 months after the initial procedure. The only difference was that the laser application was increased to applying the laser from 3 different axes focused on the substantial nigra on each side for 3 minutes each. One axis is from the lateral side of the brain parallel to the floor of the skull, the second from the top of the head, and the third roughly halfway between these. After the third procedure the patient has retained overall improvement for 10 months of follow up.

Case Study 6: Laser Guided Stem Cell Therapy to Improve Amyotrophic Lateral Sclerosis (ALS)

Patient: 69 year old white female diagnosed with the aggressive bulbar variant of ALS 6 months before. For 1-1.5 years she noted arm and leg weakness, right more than left, and arms with more weakness than her legs. She was unable to take off a shirt or dry her back with a towel. For 6 months she noted progressive and debilitating worsening of speech and swallowing functions. She also experienced pooling of saliva with occasional drooling, and would use saliva extractor if pooling excessive. She had to avoid buns and soft bread due to their tendency to get stuck. Over the preceding year she had lost 40 pounds. She also complained of mid to upper thoracic pain, and an MRI one year before had shown for aminal narrowing with moderate to severe degree of C3 through C6 spinal segments.

Her examination showed a woman who was very thin with relatively diminished body fat and muscle mass. Her neurological assessment showed slurred speech that was soft and hard to hear. She had difficulty protruding and controlling her tongue direction. Arm strength was reduced to 2-3/5 on the right and 3-4/5 on the left. Leg strength was 3/5 on the right proximally and distally and 4/5 on the left proximally and distally. Deep tendon reflexes were depressed on the right compared to the left, possibly due simply to weakness. The relaxation phase of her right ankle jerk reflex was slowed.

Procedure: The laser configuration was 674 nm modulated at 10 MHz, passed through a 5× beam expander and then phase conjugated through a SONG device from 1.28 to 0.53 mW.

There were 2 containers of cord blood stem cells (CBSCs) one of 2 ml with 50 million CBSCs and the other with 9 ml containing 100 million CBSCs. The containers were treated with the laser slowly turning them in front of the beam while moving the containers up and down for 3 minutes each.

The larger container of cells was used to inject paraspinal hotspots of inflammation at the following vertebral levels: C6, T2, T4, T12, L1, L2, L4, and L5. Injection of the right C6 area was associated with intense pain during and for several minutes after the injection. Discomfort was mild with the injection of the other paraspinal areas. Two-thirds of the 100 million cells were used for this purpose, the 33 million cells not used combined with the syringe containing 50 million cells. The 83 million cells thus derived were injected after sterile prep and anesthesia intrathecally via lumbar puncture.

The laser was scanned over the brain stem area, cervical spine and upper thoracic spine in slow sweeps dorsally from superior to inferior, then inferior to superior aspects of this zone, at about 1-2 cm per second, for a total of 8 minutes. The lumbar puncture and application of the laser were well tolerated and free of any significant adverse effects.

Results: About 10 minutes after the protocol her neurologic status was reassessed with remarkable improvements already evident. Her speech was already somewhat stronger and clearer with better control of her tongue movement and protrusion. In particular, she demonstrated and noted that her ability to articulate and differentiate the letter "m" and the letter "n" was much better. Her right arm strength had improved to be nearly equal to that of her left. The relaxation phase of her right ankle jerk reflex was less slowed.

A metabolic program to assist in clearing elevated lead and mercury levels was begun. She continued to do well with sustained improvement for 6 weeks, awaiting reduction of metals for another treatment cycle.

Case Study 7: Laser Guided Stem Cell Therapy to Regenerate Cartilage

Patient: A 73 year old white female injured her right knee in a kayaking accident, suffering multiple small tears of her medial meniscus. She had pain and limitation of movement for several months before the treatment. Exam of the knee showed full range of motion, mild tenderness to palpation of the medial patellar area, and mild crepitance. There was no effusion and neurovascular exam and ligaments were intact.

Procedure: 30 ml of fat from the medial thigh areas was harvested and then processed to yield a concentrate of adipose tissue derived mesenchymal stem cells. About 60 ml of peripheral blood was removed and processed to concentrate stem cells, much as in Example 2. This resulted in 3 containers of mesenchymal adipose derived cells and 2 containers of peripheral blood derived stem cells of 6-8 ml each.

The laser configuration was 674 nm modulated at 10 MHz, passed through a 5× beam expander and then phase conjugated through a SONG device from 1.36 to 0.52 mW. The containers were treated with the laser slowly turning them in front of the beam while moving the containers up and down, the mesenchymal adipose derived cells for 3 minutes each and the peripheral blood derived stem cells for 2 minutes each.

After sterile prepping and draping and local anesthesia the right knee was injected with, in sequence, the following:

7 ml adipose derived mesenchymal stem cells (MSCs)
7 ml peripheral blood derived stem cells (PBSCs)
7 ml MSCs
7 ml PBSCs
7 ml MSCs The laser was applied in slow sweeps over the right anterior knee side to side and up and down over the lower half of the knee at about 1 cm per second for 5 minutes. The procedure was well tolerated with no discomfort right knee for one hour after the procedure.

This entire process was repeated twice more at one month intervals for a total of 3 sessions. All of the procedures were well tolerated and free of any significant adverse effects.

Results: four months following the last procedure she was usually pain free with only occasional discomfort with weight bearing. Her exam had improved with tenderness to palpation absent and crepitance reduced to minimal. Follow up MRI scan showed that most of the medial meniscus tears had fully healed with a few minimal residual defects not considered clinically significant.

Case Study 8: Laser Guided Stem Cell Therapy to Treat Spinal Cord Injury

Patient: Middle aged male former chief of police. Patient received upper thoracic injury in an incident leading to no motor function or sensation below upper back.

Treatment and Results:

First treatment about 7 months after injury
Persistent non healing sacral ulcer of three months duration completely healed within ten days of treatment.
Noted return of partial erectile function
Over 6 weeks spinal sensory level improved 15 cm down front of chest and back
During 2nd treatment (6 weeks after first) he felt sensation in his abdomen and legs, and felt the IV needle enter his foot
Two weeks later he began to wiggle his toes with plantar stimulation Case Study 9: Laser Guided Stem Cells to Treat Stroke Patient: Middle aged male with diabetes. Stroke six years before with claw right hand and densely numb right arm and hand not improved for years. Also T4 spinal injury 30 years before with no change since then complicated by pain/spasm Treatment and Results:

Within 1 hour of treatment movement of fingers with return of sensation right hand.
Within 2 hours playing "Moonlight Sonata" for the first time in six years.
After 24 hours nearly full function of right hand and arm with spinal sensory level improved 3-5 cm front and back.
Painful muscle spasms much reduced with first 24 hours.
After 6 weeks spinal sensory level remarkably improved to low back.

Case Study 10: Laser Guided Stem Cells to Improve Cardiac Function

The great excitement and hope about stem cell therapy is the potential to rebuild the structure and function of the heart as opposed to just fighting to control symptoms, which is a fight that over time tends to be a losing battle. While there are many causes and types of heart failure, the commonest origin is damage to the muscle from ischemic heart disease and hypertension. Ischemia means insufficient blood supply to the heart generally from narrowing of the coronary arteries, though vascular spasm can sometimes cause ischemic damage even if the arteries are of normal caliber. Hypertension puts mechanical strain on the walls of the heart that can overtax muscle and lead to loss of function. Once heart muscle cells and the related contractile force they provide is lost, in general the loss has been permanent. As the heart pump weakens, the heart chambers dilate and the percentage of blood the heart can eject with each beat drops. The greater the dilation of the chambers, and the more the percentage of ejected blood diminishes, the more severe the clinical symptoms become.

The great appeal of stem cell therapy is the potential to rebuild the cellular structure and mechanical capacity of the heart muscle itself. While the hope has been great, the results of clinical studies have been generally disappointing. A meta-analysis is a review that compiles the results of several published clinical trials that meet inclusion criteria. As a comparator for innovations, a recent meta-analysis of studies that used cardiac catheterization to infuse stem cells directly into the arteries or muscle of the heart illustrates the challenges. One of the main questions with stem cell treatments is whether the stem cells actually arrive at the tissue that is the focus of repair. By infusing the cells into the coronary arteries that supply the heart or injecting them directly into the heart muscle, the question of whether the cells made it into the target organ was answered. Even with direct infusion, the result at six months was an average only 2.55% increase in cardiac ejection fraction, which did not achieve statistical significance. Given the general level of heart function for the study group, this represented an approximately 8% increase in overall heart function. While some patients did enjoy an improvement in heart function and enhanced quality of life, the overall result was less than anticipated with the aggressiveness of direct cardiac delivery.

In the above compiled studies, autologous cells from bone marrow were used. This resolves the potential issue of tissue-matching, as the cells were derived from the same person receiving the treatment. If stem cells adhered to the heart tissue, they could be incorporated as that person's normal tissue. The fact that the results were not stronger suggests that many cells failed to adhere, differentiate and incorporate. Without a strong signal to stick, many of the cells may have passed straight through the heart to the general circulation.

The novel features of the laser-activated and -guided stem cell therapy disclosed in the present specification overcomes these limitations and allows a less invasive procedure. The method provides pre-activation of the cells to make them more adherent to a target tissue. More significantly, a three dimensional homing signal is provided through the tissue to attract the cells to migrate where desired and then, most importantly, to adhere there. The method provides encouraging results with both autologous cells from a person, or even allogeneic cells derived from another person.

The novel systems and methods disclosed in the present specification were used in an approved clinical trial to test the safety and efficacy of this procedure in treating a severe end stage heart failure condition. In an embodiment, ten patients with severe end state heart failure condition were selected for the trials.

Ejection fraction (EF) is a common medical term that is used as a general measure of a person's cardiac function. It represents the amount of blood pumped out of left ventricle of the heart in each heartbeat. A normal person has ejection fraction in the range of 55% to 70%. Ejection fraction below 55% signifies that there might be some problem in the heart function and an ejection fraction below 40% usually represents a highly compromised systolic heart activity.

In the clinical trial mentioned above, all ten patients had less than or equal to 25% baseline EF, which means that at the start of the procedure, their cardiac function was highly compromised and they were having a severe heart failure condition.

Procedure: In the above mentioned clinical trial, exogenous stem cells generated from cord blood and placenta were used for the procedure. In an embodiment of the present specification, the unactivated stem cells were activated by treating them with laser radiation. In an embodiment, the laser configuration was 674 nm modulated at 10 MHz, passed through a 5× beam expander and then phase conjugated through a SONG device from 1.80 to 0.69 mW. The stem cells were treated in a syringe with this beam for three minutes. One of ordinary skill of art would appreciate that in embodiments of the present specification, different laser specifications and configuration of the modulating apparatus can also be used.

In an embodiment, the stem cells activated in the above process were infused into the patients by a slow IV push for a 5 minute period. Upon infusion of the activated stem cells, they were directed to the heart with a beam directed transcutaneously to the myocardium via the anterior myocardial projection from the anterior chest wall for five minutes and the lateral myocardial projection via the lateral chest wall for five minutes. The beam was directed over these respective regions in slow sweeps side to side and up and down to cover the entire myocardial region in both of these axes, with the rate about 1-2 cm per second.

The results of the clinical trial are depicted in table 600 of FIG. 6 which shows the EF factor for all the subjects at various stages during the three month period post treatment. As shown in FIG. 6, there were ten patients (Patient 1, Patient 2, . . . , Patient 9 and Patient 10) in the clinical trial and EF data for the Patient 1, Patient 2, Patient 3, Patient 4, Patient 5, Patient 6, Patient 7, Patient 8, Patient 9 and Patient 10 at different points in time is depicted in the corresponding rows 601, 602, 603, 604, 605, 607, 608, 609 and 610 respectively. The EF data for each patient was measured at six different stages: column 620 depicts the baseline EF data (at pre treatment stage); column 630 depicts the EF 1 data (at 3 days post treatment); column 640 depicts the EF II data (at 7 days post treatment); column 650 depicts the EF III data (at 30 days post treatment); column 660 depicts the EF IV data (at 60 days post treatment); and, column 670 depicts the EF V data (at 90 days post treatment). As shown in the table in FIG. 6, there is remarkable improvement in the condition of all the patients with 20% patients (Patient 2 and Patient 3) showing almost normal EF in three months after the treatment. Further, as shown in FIG. 6, there was a statistical significant improvement in EF factor for all the patients as detailed hereunder:

Patient 1—EF factor improved from 20% to 32% in three months

Patient 2—EF factor improved from 25% to 44% in three months

Patient 3—EF factor improved from 20% to 43% in three months

Patient 4—EF factor improved from 23% to approx 28~29% in three months

Patient 5—EF factor improved from 20% to 27% in three months

Patient 6—EF factor improved from 20% to 28% in three months

Patient 7—EF factor improved from 20% to 23% in three months

Patient 8—EF factor improved from 23% to 32% in three months

Patient 9—EF factor improved from 20% to 25% in three months

Patient 10—EF factor improved from 22% to 25% in three months

Figure 7:
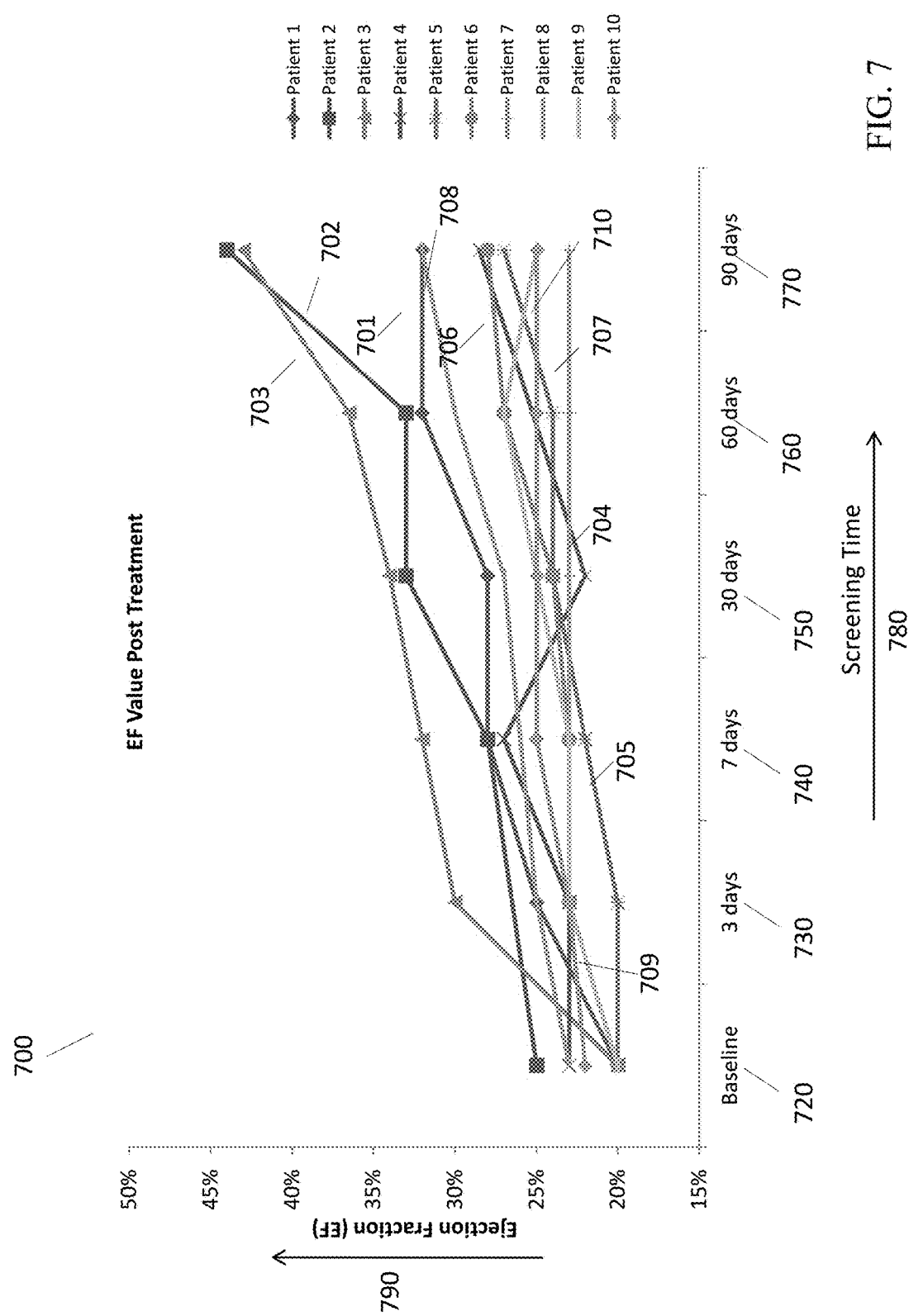
FIG. 7 illustrates a graph showing the ejection fraction value for patients participating in a clinical trial at various time intervals during the ninety day period post stem cell implantation for the treatment of an end stage heart failure condition.

The graph in FIG. 7 illustrates the EF factor recorded for the clinical trial patients at various time intervals during the ninety day period post stem cell implantation for treatment of end stage heart failure condition. In line graph 700, x-axis 780 represents the screening time and the y-axis 790 represents the EF value. The screening times at which the actual EF measurements were conducted are shown as 720 (baseline or at pre treatment stage); 730 (at 3 days post treatment), 740 (at 7 days post treatment), 750 (at 30 days post treatment), 760 (at 60 days post treatment) and 770 (at 90 days post treatment). The line graphs 701, 702, 703, 704, 705, 706.708, 709 and 710 depict the variation in EF value at various points in time for Patient 1, Patient 2, Patient 3, Patient 4, Patient 5, Patient 6, Patient 7, Patient 8, Patient 9 and Patient 10 respectively.

The patient corresponding to the line graph 701 shown in FIG. 700 is the same as the patient corresponding to row 601 mentioned in FIG. 600 and similarly any patient corresponding to the line graph 70n shown in FIG. 700 is the same as the patient corresponding to row 60n mentioned in FIG. 600 wherein n varies from 1 to 10 and represents the corresponding patient number.

The bar graph shown in FIG. 8 illustrates the net change in EF value for all the clinical trial patients ninety days post treatment. In graph 800, the x-axis 880 depicts the ten patients who participated in the clinical trial, represented as 801, 802, 803, 804, 805, 806, 807, 808, 809 and 810 respectively in the graph and the y-axis 890 depicts the net change in EF value for each patient ninety days after the treatment. The patient 801 shown in FIG. 800 is the same as the patient corresponding to row 601 mentioned in FIG. 600 and similarly any patient 80n shown in FIG. 800 is the same as the patient corresponding to row 60n mentioned in FIG. 600 wherein n varies from 1 to 10 and represents the corresponding patient number. The length of the bar corresponding to each patient represents the absolute difference in EF value recorded at the starting of the treatment and ninety days after the treatment. The graph 800 shows that there is remarkable change in EF value for all the patients; the minimum change in EF value is 3% for Patient 7 and Patient 10, and the maximum change in EF value is 23% for Patient 3.

To highlight the profundity of these clinical study results, the comparative cardiac regeneration index (CRI), defined as the percentage (%) improvement in cardiac function divided by the time (in days or other intervals) since the treatment was done, may be used. By a priori reasoning, cells given IV would have an approximate 10% chance of reaching the myocardium through random circulatory movement after infusion. The expected CRI would be at least 10 times better for the cells given by cardiac catheterization compared to cells given IV.

For stem cells directly infused or injected into the heart, in the stated large meta-analysis, the CRI was 2.55%/180 days, or 0.014% per day. In contrast, the laser guided stem cells delivered IV gave a CRI result of 14.3%/3 days, or 4.77% per day. The cardiac repair index of the laser guided approach was unexpectedly over 300 times faster than cells given by the more invasive, dangerous and expensive direct intracardiac route. After this clinical trial, the patient group achieved a 50% average increase in heart function. Approximately 50% of the patients were removed from a heart transplant list. Approximately 20% of the patients improved to a nearly normal condition. The above clinical trial represents the fastest and best stem cell results yet seen.

From the above clinical results, one may appreciate that the method and system disclosed in the present specification for delivery of stem cells for cardiac procedures is significantly superior to an invasive catheterization procedure.

A complete stem cell program comprises not only therapeutic cells activated and guided to the target location, but also the nutritional and metabolic support to deliver the greatest physiologic repair to the system. The program and support can be individually tailored to the situation of each patient while following general principles. The main rationale is to know the biochemical characteristics of the system being supported and to provide the nutrients and metabolic cofactors that best build and balance that system. Medications are continued unchanged until a person shows physiologic change that can allow adjustment of the medical regimen. After a reasonable period of observation, usually at least 2-3 months, the person is reassessed and the program can be adjusted as indicated by response.

In embodiments of the present specification, the patients are also supported nutritionally with a formula of laser-treated free amino acids. With respect to those persons with ischemic heart disease, another adjunct that is offered is a laser-treated arginine formula. This was given at a level of 1.5 grams of arginine with cofactors twice a day for one with 20 month persons with severe coronary arteries. The inclusion criteria were persons with one or more previous myocardial infarctions who had recurrence of chest pain with exertion or rest or both. The control group showed no improvement in symptoms over 30 days, whereas nutritional support was associated with a 70-80% reduction of chest pain with exertion or rest. There were cases of positive exercise tests reverting to showing no ischemia with exertion. Perhaps of greatest interest, the control group showed a 10% reduction of maximum exercise capacity whereas this was increased 60% in the active treatment group.

Case Study 11: Laser Guided Stem Cells to Regenerate Bone Joint Structures

Degeneration and diseases of joints, cartilage and tendons are among the most common conditions that cause pain, debility, and reduced quality of life. While nutrition, gentle exercise, and low grade anti-inflammatory drugs offer relief in milder cases, progressive degeneration can result in chronic severe pain relieved only with surgical repair or replacement. A new approach of using stem cells disclosed in the present specification is used to regenerate joint and tendon related structures which provides greater relief with fewer risks and better functional results compared to invasive surgery that can make a person permanently "titanium dependent."

The greatest challenge that occurs for stem cell therapy is in the condition of bone on bone joint degeneration. Once the articular cartilage is so reduced that rough bone edges grate on bone, the cushion and glide are gone and the general dictum has been that joint replacement is then required. There are three main challenges in using stem cells as a remedy in this circumstance. The first challenge is that cartilage has relatively poor circulation and vascularity. This is a major predisposing factor to degeneration in the first place with limitations on the ability to bring nutrients and repair cells to the joint surface. The second challenge is that the chronic inflammatory processes resulting as cartilage wears and bone spurs accelerates the tendency for further cartilage loss. Once the cartilage has been completely stripped from the joint surface bone grating on bone is a destructive process that can leave bits of bone in the joint space that further irritate and aggravate the process.

Joint replacement, especially of knees and hips, has become a relatively common intervention. While this may relieve pain and improve function for badly degenerated joints and cartilage, there is no going back after the native structures have been altered with foreign material. Any surgical procedure may be complicated by pain, bleeding and infection. The occurrence of infection can be particularly catastrophic with the need to remove the appliance along with prolonged hospitalization and antibiotics to clear the infection from bone, which can be difficult and in some cases impossible. The mechanical solution can also be less than desired with chronic residual pain despite the procedure. Range of motion and function, while often better after replacement, may not be as good as the results of restoring function to the native joint as now may be possible.

Laser activated and guided stem cell therapy as disclosed in the present specification, combined with nutritional and metabolic support, improves the outcome compared to surgery and regenerate healthy functional joint, cartilage and tendon structures. While procedures for joints and tendons often allow localized injection into joint spaces and tendon areas, the ability of the laser platform to increase cell adhesion necessary for repair resulted in improvement in symptoms and functional results that are better and faster than expected with just the local injection of stem cells. For example, one middle aged male patient who had suffered seven right sided shoulder dislocations during a college wrestling match had suffered chronic pain and restricted motion for 35 years after the injury. A surgical procedure was done which increased stability and reduced symptoms but further restricted range of movement. He had received multiple injections of platelet rich plasma without significant relief. In embodiments of the present specification, using the protocol of autologous stem cells from his blood activated with the laser and then infused IV and injected intra-articularly (from a posterior approach) followed by laser guidance into the joint and peri-articular tissue the results were astonishing. Immediately after the laser was applied to the right shoulder area the pain was essentially completely gone and his previously restricted range returned to normal.

In another case study involving the usage of laser activation and guidance method described in the present specification, a right hip in a middle aged male caused chronic up to 8-10/10 pain with weight bearing after prolonged sitting. MRI scan showed loss of articular cartilage as well as a tear of the labrum, or lip of the hip joint capsule. In this case the cells were only injected IV and guided to the hip with the laser without any direct injection of the joint. Immediately after the laser guidance the range of movement improved to normal and the pain was resolved. In the next 2 weeks there was only one episode of mild pain with standing up after prolonged sitting, compared to the usual severe pain with that would occur every time in that circumstance.

Lesser degrees of joint, tendon, and cartilage injury also tend to respond well and quickly to the laser activation and guidance approach disclosed in the present specification. With this method the stem cells are infused IV which can then optionally be locally augmented with intra-articular, peri-articular, and peri-tendinous injection. The deeply penetrating, stem cell attracting, and adherence amplifying laser technology disclosed in the present specification when applied to the affected area recruits cells to the surrounding support tissue while enhancing adherence of stem cells to the specific tissues to be rebuilt, regenerated and structurally and functionally restored.

As a complex structural and biochemical systems, articular cartilage and bone, tendons and ligaments, and other connective tissues require many support nutrients for optimal repair and function. In embodiments of the present specification, the laser activated and guided stem cell therapy is combined along with individualized nutrient protocols to support accelerated recovery. For example, for the pain and inflammation of degenerative arthritis, the clinically validated formula FLEX JC was effective for relieving pain in 80% of persons and eliminated X-ray evidence of inflammation in 85% of persons taking it for one month, which was significantly better than for the untreated control group.

For a given musculoskeletal problem, a nutritional metabolic program is recommended. Subsequently, the optimum source and route of delivery of cells is determined. In most cases this will simply be autologous blood derived repair cells, though autologous mesenchymal fat or allogeneic cells are also used in embodiments. After a given treatment, improvement can continue for as long as three months or more, at which time there would be an assessment of whether the healing is complete or whether any additional treatment or adjustment of protocol is required.

In embodiments of the present specification, though significant improvements were achieved within 24 hours using autologous stem cells from fat or bone marrow, or allogeneic stem cells from umbilical cord blood, the most promising source appears to be the fresh autologous blood. The systems and methods disclosed in the present specification have the ability to stimulate tiny otherwise dormant repair cells in the blood stream to become active provides a ready source of ideally matched cells. Once activated, in vitro studies have shown these repair cells can become cartilage, bone and tendon and virtually every other cell line of the body, depending on the cellular environment in which they are placed. In their state of dormancy, these cells appear to maintain the telomere lengths of a newborn. This source of autologous cells is not only less invasive than extracting a person's fat or bone marrow, they also appear to be more robust that from these sources, especially if the person is older biologically.

Laser Guided Stem Cells to Treat Diabetic Condition

In an embodiment, the systems and methods disclosed in the present specification are used for treating a diabetic condition. Diabetes and the metabolic syndrome are reaching epidemic proportions in the developed world and the developing world is echoing this rapid increase in global prevalence. As an index of the magnitude of the problem, in the US in 2012, there were 29.1 million adults representing about 9.3% of the population with Type-2 diabetes. At that time there were also 1.25 million children and adults with Type-1 diabetes. The estimated cost of diagnosed diabetes in 2012 was $245 billion in US, with $176 billion in direct costs and $69 billion in the form of reduced productivity.

While stem cells have shown encouraging results in the past in reducing the adverse effects of diabetes, the systems and methods disclosed in the present specification have shown promising results in using stem cells for the treatment of the actual diabetic condition. In an embodiment, the systems and methods disclosed in the present specification are used to stimulate the dormant repair cells in the blood such that these cells become highly functional with the vitality of young stem cells. In an embodiment, the stem cells are used to improve the pancreatic function which helps in reversing the Type-2 diabetes. Rather than requiring invasive and potentially dangerous angiographic localization and infusion of stem cells into the pancreatic bed by way of the celiac artery, the laser activation and guidance method described in the present specification only requires an intravenous administration. The stem cells are directed to the pancreas using a low energy beam safely applied through the skin. In embodiments, a laser guidance signal is used that attracts the stem cells to the specific region in the tissue that requires the therapy. The laser signal further stimulates the stem cells and enhances their activity level and the adhesiveness which supports their integration in the location they are directed. In another embodiment, tissues that have sustained complications of diabetes such as the tissues in eyes, heart and kidneys are also treated by directing reparative stem cells in such tissues with the help of a laser beam. In embodiments, the power level of the laser signal is gentle such that it neither heats nor hurts the tissue. In an embodiment, a laser signal with a wavelength of 674 nm is used such that the individual photon energy is well below the level that can cause ionization. In embodiments of the present specification, the wavelength and related energy density of laser beams are well within the levels accepted as safe by the US FDA.

In an embodiment of the present specification, in selected cases, the laser-activated and -guided stem cell therapy as described in the present specification is used along with the pulsed intravenous insulin therapy (PIVIT) to treat the diabetic condition. The pulsed intravenous insulin therapy (PIVIT) protocol provides pulsatile infusions of insulin calibrated to body weight over a few hour intravenous sessions. This process mimics the healthy physiologic impulses of insulin that reach the liver through the portal circulation from the pancreas after a carbohydrate meal. This pulsation resets and recalibrates the liver function to enhance the body's response to insulin and lower insulin resistance. For Type-2 diabetes, after a series of 10-12 sessions over a several week period, insulin sensitivity is greatly increased, improving blood sugar levels and reducing medication requirements. In type 1 diabetes, weekly sessions have shown positive results in clinical studies with significant reduction in the risk of long term complications of retinopathy, peripheral neuropathy and nephropathy.

In embodiments of the present specification, targeted nutritional supplementation is used which helps in improving the results. A laser-activated formula containing L-carnitine and acetyl-L-carnitine, was shown to reduce body weight by about 6 pounds (2.7 Kg) in a month if taken alone, or by 10 pounds (4.5 Kg) in a month if combined with walking briskly 30 minutes daily. Average caloric intake was also reduced by 300 calories per day. These nutrients have been shown to reduce the adverse effects of hyperglycemia-related tissue glycation (sugars being bound chemically where they don't belong), a major cause of long-term tissue pathology. It is well known that weight reduction in type 2 diabetes can reduce blood sugars and increase glycemic control, even to the point of clinical remission.

In Type 1 diabetes, there is an absolute deficiency of insulin due to the loss of beta cells in the pancreas rather than insulin resistance. In embodiments, the systems and methods of the present specification is used for the treatment of Type-1 diabetes. Autologous stem cells of varying types have shown the effect of immune modulation and balancing. This treatment is being explored to reduce the intensity and complications of the major auto-immune diseases such as rheumatoid arthritis. The above use of stem cells has the potential to curb or reduce the auto-immunity of Type-1 diabetes that selectively destroys the insulin secreting beta cells of the pancreas. In an embodiment, the laser activation and guidance method described in the present specification is used for replacing the lost beta cells in a safe and effective manner by guiding the laser activated stem cells to populate and function in the pancreas.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method of repairing damaged biological tissue comprising:
    obtaining unactivated stem cells;
    forming activated stem cells from the unactivated stem cells by treating the stem cells with an amplitude modulated laser beam having a pre-defined wavelength and a pre-defined amplitude;
    administering the activated stem cells into a body containing the biological tissue;
    transcutaneously applying a homing coherent laser beam along a first axis such that the homing coherent laser beam interacts with said damaged biological tissue; and
    transcutaneously applying the homing coherent laser beam along a second axis such that the homing coherent laser beam interacts with the damaged biological tissue, wherein the first axis and the second axis intersect at the damaged biological tissue and point at different directions relative to each other.

2. The method of claim 1 wherein the homing coherent laser beam is generated using a 20% to 90% phase cancellation.

3. The method of claim 1 wherein the unactivated stem cells are harvested from an autologous source including at least one of peripheral blood, bone marrow, or fat.

4. The method of claim 1, wherein the unactivated stem cells are harvested from an exogenous source including at least one of a cord blood and a placenta of the patient.

5. The method of claim 1, wherein the unactivated stem cells are sourced from a genetically matched stem cell donor.

6. The method of claim 1 wherein the pre-defined wavelength is in a range of 405 to 980 nanometers.

7. The method of claim 1 wherein the amplitude modulated laser beam has a wavelength of 674 nanometers.

8. The method of claim 1, wherein the amplitude modulated laser beam comprises a string of short duration pulses of sub-femto second duration.

9. The method as claimed in claim 1 wherein, prior to treating the unactivated stem cells, the amplitude modulated laser beam is expanded in a range varying between two times to seven times by passing the amplitude modulated laser beam through a beam expander.

10. The method as claimed in claim 1 wherein, prior to treating the unactivated stem cells, the amplitude modulated laser beam is passed through a Strachan-Ovokaitys Node Generator.

11. The method as claimed in claim 1 wherein a phase cancellation of the amplitude modulated laser beam is adjusted to achieve a predetermined power output before treating the unactivated stem cells.

12. The method as claimed in claim 11 wherein the unactivated stem cells are positioned in a container and wherein the container is rotated at a speed of one rotation in every 3 to 5 seconds and is moved up and down for a duration of 15 seconds in each direction.

13. The method as claimed in claim 1 wherein treating the unactivated stem cells comprises applying the amplitude modulated laser beam to a container containing the unactivated stem cells such that the container is rotated and simultaneously moved up and down in a vertical direction during the activation process.

14. The method as claimed in claim 1 wherein treating the stem cell is with the amplitude modulated laser beam is done such that, relative to the unactivated stem cells, the activated stem cells comprise at least one of an increased expression of an alpha or beta integrin, an increase in CD34, or an enhanced migratory action in a direction of the homing coherent laser beam.

15. The method of claim 1 wherein the biological tissue is at least one of myocardial tissue, lung tissue, kidney tissue, blood vessels, immune system cells, bone tissue, teeth, liver tissue, endocrine tissues, pituitary tissue, thymus tissue, intervertebral discs, brain tissue, spinal tissue, pancreatic tissue and nerve tissue.

16. A method of treating damaged cardiac tissue of a patient comprising:
    obtaining unactivated stem cells;
    forming activated stem cells from the unactivated stem cells by treating the stem cells with an amplitude modulated laser beam having a pre-defined wavelength and a pre-defined amplitude;
    intravenously administering the activated stem cells into the patient;
    transcutaneously applying a homing laser beam along a first axis such that the homing laser beam interacts with said cardiac tissue; and
    transcutaneously applying the homing laser beam along a second axis such that the homing laser beam interacts with the cardiac tissue, wherein the first axis and the second axis intersect at the cardiac tissue and point at different directions relative to each other.

17. The method of claim 16 wherein the homing laser beam is generated using a 20% to 90% phase cancellation.

18. A method of treating a neurological condition in a patient comprising:
    obtaining unactivated stem cells;
    forming activated stem cells from the unactivated stem cells by treating the stem cells with an amplitude modulated laser beam having a pre-defined wavelength and a pre-defined amplitude;
    intravenously administering the activated stem cells into the patient;
    transcutaneously applying a homing coherent laser beam along a first axis such that the homing coherent laser beam interacts with brain tissue and/or spinal cord tissue of the patient; and
    transcutaneously applying the homing coherent laser beam along a second axis such that the homing coherent laser beam interacts with the brain tissue and/or spinal cord tissue, wherein the first axis and the second axis intersect at the brain tissue and/or spinal cord tissue and point at different directions relative to each other.

19. The method of claim 18 wherein the homing coherent laser beam is swept over said spinal cord tissue and swept over said brain tissue.

20. The method of claim 19 wherein the homing coherent laser beam is generated using a 20% to 90% phase cancellation.

\* \* \* \* \*